US012616570B2

(12) United States Patent
Anderson et al.

(10) Patent No.: US 12,616,570 B2
(45) Date of Patent: May 5, 2026

(54) THREE-DIMENSIONAL THIN-FILM LEAFLET VALVE DEVICE

(71) Applicant: Nininger Medical, Inc., Houston, TX (US)

(72) Inventors: Daniel Corey Anderson, Houston, TX (US); Lowie Michel Roger Van Assche, Miami, FL (US); Hussain Soaeb Rangwala, Villa Park, CA (US); Christopher S. Malaisrie, Chicago, IL (US)

(73) Assignee: Nininger Medical, Inc., Houston, TX (US)

( * ) Notice: Subject to any disclaimer, the term of this patent is extended or adjusted under 35 U.S.C. 154(b) by 855 days.

(21) Appl. No.: 17/916,543

(22) PCT Filed: Apr. 1, 2021

(86) PCT No.: PCT/US2021/025441
§ 371 (c)(1),
(2) Date: Sep. 30, 2022

(87) PCT Pub. No.: WO2021/202916
PCT Pub. Date: Oct. 7, 2021

(65) Prior Publication Data
US 2023/0157817 A1     May 25, 2023

Related U.S. Application Data

(60) Provisional application No. 63/003,840, filed on Apr. 1, 2020.

(51) Int. Cl.
*A61F 2/24* (2006.01)

(52) U.S. Cl.
CPC .......... *A61F 2/2418* (2013.01); *A61F 2/2415* (2013.01); *A61F 2220/0008* (2013.01); *A61F 2230/0013* (2013.01); *A61F 2230/008* (2013.01)

(58) Field of Classification Search
CPC .... A61F 2/2412; A61F 2/2418; A61F 2/2475; A61F 2/2476
See application file for complete search history.

(56) References Cited

U.S. PATENT DOCUMENTS 5,509,930 A * 4/1996 Love ...................... A61F 2/2412
623/900
5,713,953 A * 2/1998 Vallana ................. A61F 2/2412
623/2.15
(Continued)

FOREIGN PATENT DOCUMENTS

CN        105307598 B  *  9/2017  ........... A61F 2/2415
CN     109 475 411         3/2019
(Continued)

OTHER PUBLICATIONS

Bechtold et al., "Capability of sputtered micro-patterned NiTi thick films," Shape Memroy and Superelasticity (2015) 1:286-293.
(Continued)

*Primary Examiner* — Alvin J Stewart
(74) *Attorney, Agent, or Firm* — MORRISON & FOERSTER LLP

(57) ABSTRACT

Examples of the disclosure are directed toward a valve device comprising an opening and a leaflet and methods of operating and manufacturing the valve device. In some embodiments, the leaflet is a three-dimensional thin-film leaflet, and the leaflet comprises a dome portion. In a first configuration, the leaflet of the valve device may occlude the opening of the device. In a second configuration, the leaflet may not occlude the opening, and blood may flow across the
(Continued)

opening of the device. The valve device may be collapsible for transportation in a catheter.

17 Claims, 12 Drawing Sheets

(56) References Cited

U.S. PATENT DOCUMENTS

| | | | |
|---|---|---|---|
| 6,666,885 B2 | 12/2003 | Moe | |
| 7,799,069 B2 | 9/2010 | Bailey et al. | |
| 7,803,186 B1* | 9/2010 | Li | A61F 2/2418 |
| | | | 623/2.18 |
| 8,460,361 B2 | 6/2013 | Whitcher et al. | |
| 8,500,799 B2 | 8/2013 | Forster et al. | |
| 8,556,960 B2* | 10/2013 | Agnew | A61L 27/3604 |
| | | | 623/1.24 |
| 9,480,559 B2 | 11/2016 | Vidlund et al. | |
| 9,737,398 B2 | 8/2017 | Bruchman et al. | |
| 9,839,511 B2 | 12/2017 | Ma et al. | |
| 10,052,204 B2* | 8/2018 | McLean | A61F 2/2427 |
| 10,172,710 B2* | 1/2019 | Drasler | A61F 2/2433 |
| 10,368,982 B2 | 8/2019 | Weber et al. | |
| 10,617,519 B2 | 4/2020 | Vidlund et al. | |
| 10,639,145 B2 | 5/2020 | Vidlund et al. | |
| 11,278,396 B2* | 3/2022 | Moore | A61F 2/2427 |
| 2003/0078652 A1* | 4/2003 | Sutherland | A61F 2/2412 |
| | | | 623/2.12 |
| 2005/0137681 A1* | 6/2005 | Shoemaker | A61F 2/06 |
| | | | 623/1.23 |
| 2005/0137682 A1* | 6/2005 | Justino | A61F 2/2418 |
| | | | 623/2.14 |
| 2006/0058872 A1* | 3/2006 | Salahieh | A61F 2/2412 |
| | | | 623/1.36 |
| 2006/0232374 A1* | 10/2006 | Johnson | B81B 3/0072 |
| | | | 338/308 |
| 2009/0105813 A1* | 4/2009 | Chambers | A61F 2/2412 |
| | | | 623/2.38 |
| 2009/0276039 A1* | 11/2009 | Meretei | A61F 2/2418 |
| | | | 623/2.22 |
| 2010/0256723 A1 | 10/2010 | Murray et al. | |
| 2011/0098802 A1* | 4/2011 | Braido | A61F 2/243 |
| | | | 623/2.11 |
| 2012/0121657 A1 | 5/2012 | Zhou et al. | |
| 2012/0185038 A1* | 7/2012 | Fish | A61F 2/2415 |
| | | | 493/405 |
| 2013/0184813 A1 | 7/2013 | Quadri et al. | |
| 2013/0274874 A1* | 10/2013 | Hammer | A61F 2/2439 |
| | | | 623/2.12 |
| 2013/0304196 A1* | 11/2013 | Kelly | A61F 2/2475 |
| | | | 623/1.25 |
| 2014/0222136 A1* | 8/2014 | Geist | A61F 2/2436 |
| | | | 623/2.37 |
| 2015/0164636 A1* | 6/2015 | Valdez | A61F 2/2412 |
| | | | 623/2.19 |
| 2015/0164662 A1* | 6/2015 | Tuval | A61F 2/2418 |
| | | | 623/1.24 |
| 2017/0056163 A1* | 3/2017 | Tayeb | A61F 2/2415 |
| 2017/0189172 A1* | 7/2017 | Grundeman | A61F 2/2412 |
| 2017/0340463 A1* | 11/2017 | Chun | A61L 31/088 |
| 2018/0021129 A1* | 1/2018 | Peterson | A61F 2/2409 |
| | | | 623/2.17 |
| 2018/0177591 A1* | 6/2018 | Valdez | A61F 2/2412 |
| 2018/0200050 A1 | 7/2018 | Bruchman et al. | |
| 2018/0360599 A1 | 12/2018 | Drasler et al. | |
| 2019/0053803 A1 | 2/2019 | Ketai et al. | |
| 2019/0069996 A1 | 3/2019 | Saar et al. | |
| 2020/0163761 A1* | 5/2020 | Hariton | A61F 2/2412 |
| 2020/0360135 A1* | 11/2020 | Hofferberth | A61F 2/2433 |
| 2021/0290384 A1 | 9/2021 | Manash | |
| 2022/0218472 A1* | 7/2022 | Morriss | A61F 2/2445 |
| 2024/0138979 A1* | 5/2024 | Quill | A61F 2/2418 |
| 2024/0225820 A1* | 7/2024 | Leonardi | A61F 2/2409 |
| 2024/0415643 A1* | 12/2024 | Sands | A61F 2/2439 |
| 2025/0009501 A1* | 1/2025 | Salehyar | A61F 2/2418 |
| 2025/0268712 A1* | 8/2025 | Hariton | A61F 2/2409 |

FOREIGN PATENT DOCUMENTS

| | | |
|---|---|---|
| JP | 2009-540955 | 11/2009 |
| JP | 2016-535650 | 11/2016 |
| JP | 2020-022782 | 2/2020 |
| WO | WO 2005/007018 | 1/2005 |
| WO | WO 2007/095233 | 8/2007 |
| WO | WO 2012/177942 | 6/2012 |
| WO | WO 2013/059743 | 4/2013 |
| WO | WO 2015/061496 | 10/2014 |
| WO | WO 2017/201082 | 11/2017 |
| WO | WO 2019/094181 | 5/2019 |

OTHER PUBLICATIONS

Levi et al., "Smart Materials Applications for Pediatric Cardiovascular Devices," Pediatr Res (2008) 63:552-558.
Loger et al., "Cell adhesion on NiTi thin film sputter-deposited meshes," Materials Science and Engineering C 59(2016) 611-616.
Loger et al., "Fabrication and Evaluation of Nitinol Thin Film Heart Valves," Cardiovascular Engineering and Technology (2014) 5(4):308-316.
Loger et al., "Microstructured Nickel-Titanium Thin Film Leaflets for Hybrid Tissue Engineered Heart Valves Fabricated by Magnetron Sputter Deposition," Cardiovascular Engineering and Technology (2016) 7(1):69-77.
Sizarov et al., "Novel materials and devices in the transcatheter management of congenital heart diseases-the future comes slowly (part 3)," Archives of Cardiovascular Disease (2016) 109:348-358.
Shayan et al., "An overview of thin film nitinol endovascular devices," Acta Biomaterialia (2015) 21:20-34.
Stepan et al., "A thin film nitinol heart valve," 2004 ASME International Mechanical Engineering Congress and Exposition, Nov. 13-20, 2004, Anaheim, California USA.

* cited by examiner

200

202

210

202

206

206

250

252

314

316

Atrium

Native
Valve
Leaflet

366

368

Chordae
Tendinae

Ventricle

Papillary
Muscle

THREE-DIMENSIONAL THIN-FILM LEAFLET VALVE DEVICE

CROSS REFERENCE TO RELATED APPLICATIONS

This application is a national stage application under 35 U.S.C. § 371 of International Application No. PCT/US2021/025441, filed internationally on Apr. 1, 2021, which claims benefit of U.S. Provisional Application No. 63/003,840 filed Apr. 1, 2020, the entire disclosures of which are herein incorporated by reference for all purposes.

FIELD OF THE INVENTION

This disclosure generally relates to medical devices. More specifically, this disclosure relates to artificial valves.

BACKGROUND OF THE INVENTION

More than 1.6 million patients in the United States may need treatment for moderate to severe tricuspid regurgitation (TR). The presence of moderate to severe TR may be associated with poor prognosis, with as many as 36% of patients dying within one year. However, given the high mortality and morbidity of surgical tricuspid valve repair or replacement, only 8,000 surgeries are performed. Therefore, there is currently an unmet need for the treatment of these patients.

For example, known transcatheter tricuspid valves cannot be reliably compressed and delivered to the anatomic location. Design limitations exist in both the valve leaflets and the valve frame supporting the leaflets. Further, these known designs are expensive to manufacture and prone to failure when deployed.

For at least these reasons, a more reliable, a more cost-effective, and a more durable valve device is sought.

SUMMARY OF THE INVENTION

Examples of the disclosure are directed toward a valve device comprising an opening and a leaflet and methods of operating and manufacturing the valve device. In some embodiments, the leaflet is a three-dimensional thin-film leaflet, and the leaflet comprises a dome portion. In a first configuration, the leaflet of the valve device may occlude the opening of the device. In a second configuration, the leaflet may not occlude the opening, and blood may flow across the opening of the device. The valve device may be collapsible for transportation in a catheter.

In some embodiments, a valve device, comprises: an opening, and a leaflet comprising: a downstream surface to trap blood pumped by a heart muscle, and an upstream surface to selectively occlude the opening when the leaflet's downstream surfaces trap blood pumped by the heart muscle.

In some embodiments, the leaflet is a three-dimensional thin-film leaflet.

In some embodiments, the upstream surface comprises a dome portion.

In some embodiments, a shape of the leaflet includes a plurality of profiles, each profile includes dimensions of an interfacing surface height, an outer cylindrical surface height, and a profile slope angle, and the profile slope angle is associated with geometries of the dome portion.

In some embodiments, the interfacing surface height is 2-10 mm, the outer cylindrical surface height is 3-25 mm, and the profile slope angle is −45 to 45 degrees.

In some embodiments, the shape of the leaflet includes a dimension of an average slope associated with an average of at least some of the profile slope angles along at least a part of a depth of the leaflet, and the average slope is 0 to 45 degrees.

In some embodiments, the device consists three leaflets.

In some embodiments, the device further comprises a second leaflet, wherein the leaflets' upstream surfaces collectively occlude the opening when the leaflets are in a first configuration, and the upstream surfaces do not collectively occlude the opening when the leaflets are in a second configuration.

In some embodiments, each leaflet comprises an interfacing surface that, while the leaflets occlude the opening, contacts an adjacent leaflet's interfacing surface.

In some embodiments, the interfacing surface has a height of 2-10 mm.

In some embodiments, the interfacing surface comprises ridges and troughs.

In some embodiments, the ridges and troughs are parallel to a direction from the upstream surface to the downstream surface.

In some embodiments, the interfacing surface comprises dimples located periodically along the interfacing surface.

In some embodiments, the interfacing surface comprises cuts.

In some embodiments, a thickness along a surface of the leaflet is non-uniformed.

In some embodiments, the device further comprises a frame, wherein a portion of the leaflet attaches to the frame, the portion comprising a non-uniform thickness.

In some embodiments, the leaflet has a thickness of 5-250 μm.

In some embodiments, the device comprises a collapsed configuration such that the device in the collapsed configuration is deliverable in a catheter having a cross sectional diameter of 5-15 mm.

In some embodiments, the leaflet comprises at least one of biocompatible alloy, polymer, and composite structure.

In some embodiments, the leaflet is fabricated using vacuum deposition, physical vapor deposition (PVD), or chemical vapor deposition (CVD).

In some embodiments, the leaflet comprises: a first configuration in response to a force from the downstream side to the upstream side, and a second configuration in response to a force from the upstream side to the downstream side.

In some embodiments, the first configuration is a closed configuration and the second configuration is an open configuration.

In some embodiments, the force from the downstream side to the upstream side includes a force generated by an increase of the blood being trapped.

In some embodiments, the leaflet collapses in response to the force from the upstream side to the downstream side.

In some embodiments, the leaflet returns toward an inflated shape in response to an increase of the blood being trapped.

In some embodiments, the leaflet further includes stress relief features.

In some embodiments, the stress relief features are formed using at least one of laser cutting, photo-lithography, vapor deposition, hot-working, cold-working, photo-etching, and mechanical cutting.

In some embodiments, the leaflet is deformable under applied pressure and return to an inflated shape after the pressure is removed.

In some embodiments, the leaflet is formed by physical vapor deposition of at least one of an alloy and a polymer.

In some embodiments, the alloy is superelastic Nitinol.

In some embodiments, the polymer is Kevlar, Parylene, Polytetrafluoroethylene (PTFE), or fluorinated ethylene propylene (FEP).

In some embodiments, the leaflet is formed by at least one of dipping, painting, and molding.

In some embodiments, the downstream surface is a domed surface along one of radial and lateral directions to reduce at least one of stress and stasis.

In some embodiments, the device further comprises a frame defining the opening, wherein the leaflet is attached to the frame.

In some embodiments, the device further comprises a skirt attached to the frame and outside the opening to occlude blood pumped by the heart muscle in a direction from the downstream surface to the upstream surface outside the opening.

In some embodiments, the frame is cylindrical and a portion of the attached leaflet matches a contour of the frame.

In some embodiments, an interfacing surface is oriented in a direction parallel to a central axis of the device.

In some embodiments, the frame is a stent frame having anchoring prongs to maintain the device at a native valve location.

In some embodiments, the frame crimps within a catheter.

In some embodiments, the anchoring prongs are in a pinching position upon contact with an underside of native leaflets.

In some embodiments, the anchoring prongs are configured to draw a valve annulus toward a center of the opening.

In some embodiments, the stent frame further includes a cord connecting the anchoring prongs, the cord to tighten and pull the anchoring prongs toward the frame as the frame expands.

In some embodiments, the cord is connected to three anchoring prongs.

In some embodiments, the device further comprises a second cord connected to three second anchoring prongs, each of the second anchoring prongs positioned on the frame and adjacent to a first anchoring prong.

In some embodiments, the cord comprises at least one of a wire rope of one of Nitinol, a wire rope of a non-Nitinol biocompatible alloy, a solid or multi-filar cord of a PTFE, a solid or multi-filar Kevlar cord, and a non-PTFE and a no-Kevlar solid or multi-filar cord.

In some embodiments, the device further comprises cord attachment points between adjacent anchoring prongs of a set of anchoring prongs.

In some embodiments, the anchoring prongs are equally-spaced along a circumference of the frame.

In some embodiments, the frame comprises a plurality of collapsible cells.

In some embodiments, the frame is created by laser cutting.

In some embodiments, the frame is balloon-expandable.

In some embodiments, a method of operating an artificial valve, comprising: in response to blood pumped by a heart muscle in a direction from a downstream surface to an upstream surface of a thin-film leaflet of the artificial valve: selectively occluding an opening of the artificial valve with the upstream surface, and trapping the blood pumped by the heart muscle with the downstream surface; and in response to blood flow in a direction from the upstream surface to the downstream surface: deforming, with a force of the blood flow, the leaflet, and allowing the blood flow across the opening.

In some embodiments, the artificial valve is the disclosed valve device.

In some embodiments, a method of implanting a valve device, comprising: collapsing the valve device to fit into a catheter; deploying the valve device from the catheter; in response to deploying the valve device from the catheter, restoring a shape of the valve device; and anchoring the valve device to a native leaflet comprising pinching the native leaflet between an anchoring prong and a frame of the valve device.

In some embodiments, the valve device is the disclosed valve device.

In some embodiments, a method of manufacturing a valve device, comprising: providing a three-dimensional thin-film leaflet comprising: a downstream surface to trap blood pumped by a heart muscle, and an upstream surface to selectively occlude an opening of the valve device when the leaflet's downstream surfaces trap blood pumped by the heart muscle; providing a frame defining an opening of the valve device, wherein the frame comprises a plurality of cells; and attaching the leaflet to the frame.

In some embodiments, providing the three-dimensional thin-film leaflet further comprises fabricating the leaflet using at least one of biocompatible alloy, polymer, and composite structure.

In some embodiments, providing the three-dimensional thin-film leaflet further comprises fabricating the leaflet using vacuum deposition, PVD, or CVD.

In some embodiments, providing the three-dimensional thin-film leaflet further comprises forming stress relief features on the leaflet using at least one of laser cutting, photo-lithography, vapor deposition, hot-working, cold-working, photo-etching, and mechanical cutting.

In some embodiments, providing the three-dimensional thin-film leaflet further comprises fabricating the leaflet using physical vapor deposition of at least one of an alloy and a polymer.

In some embodiments, the alloy is superelastic Nitinol.

In some embodiments, the polymer is Kevlar, Parylene, PTFE, or FEP.

In some embodiments, providing the three-dimensional thin-film leaflet further comprises fabricating the leaflet using at least one of dipping, painting, and molding.

In some embodiments, the method further comprises attaching a skirt to the frame outside the opening to stop blood pumped by the heart muscle in a direction from the downstream surface to the upstream surface outside the opening.

In some embodiments, providing the frame further comprises providing anchoring prongs on the frame.

In some embodiments, the method further comprises connecting a cord to the anchoring prongs.

In some embodiments, the cord comprises at least one of a wire rope of one of Nitinol, a wire rope of a non-Nitinol biocompatible alloy, a solid or multi-filar cord of a PTFE, a solid or multi-filar Kevlar cord, and a non-PTFE and a no-Kevlar solid or multi-filar cord.

In some embodiments, providing the frame further comprises laser cutting to form the frame.

In some embodiments, attaching the leaflet to the frame further comprises at least one of welding, sewing, clamping, and gluing the leaflet to the frame.

In some embodiments, the valve device is the disclosed valve device.

DETAILED DESCRIPTION OF EXEMPLARY EMBODIMENTS

In the following description of embodiments, reference is made to the accompanying drawings which form a part hereof, and in which it is shown by way of illustration specific embodiments which can be practiced. It is to be understood that other embodiments can be used and structural changes can be made without departing from the scope of the disclosed embodiments.

Examples of the disclosure are directed toward a valve device comprising an opening and a leaflet and methods of operating and manufacturing the valve device. In some embodiments, the leaflet is a three-dimensional thin-film leaflet, and the leaflet comprises a dome portion. In a first configuration, the leaflet of the valve device may occlude the opening of the device. In a second configuration, the leaflet may not occlude the opening, and blood may flow across the opening of the device. The valve device may be collapsible for transportation in a catheter.

Figure 1A:
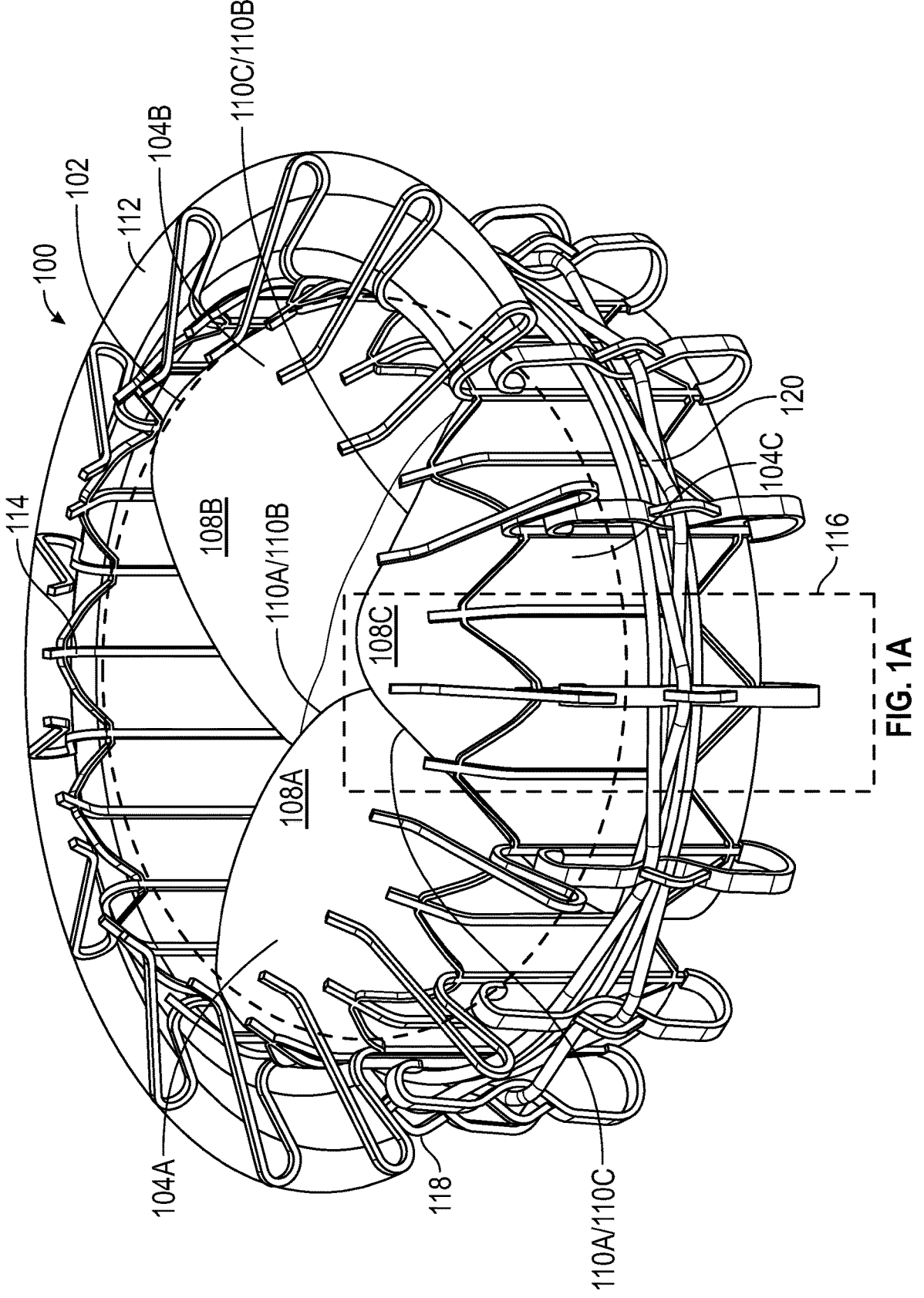
FIGS. 1A-1C illustrate an exemplary valve device.
Figure 1B:
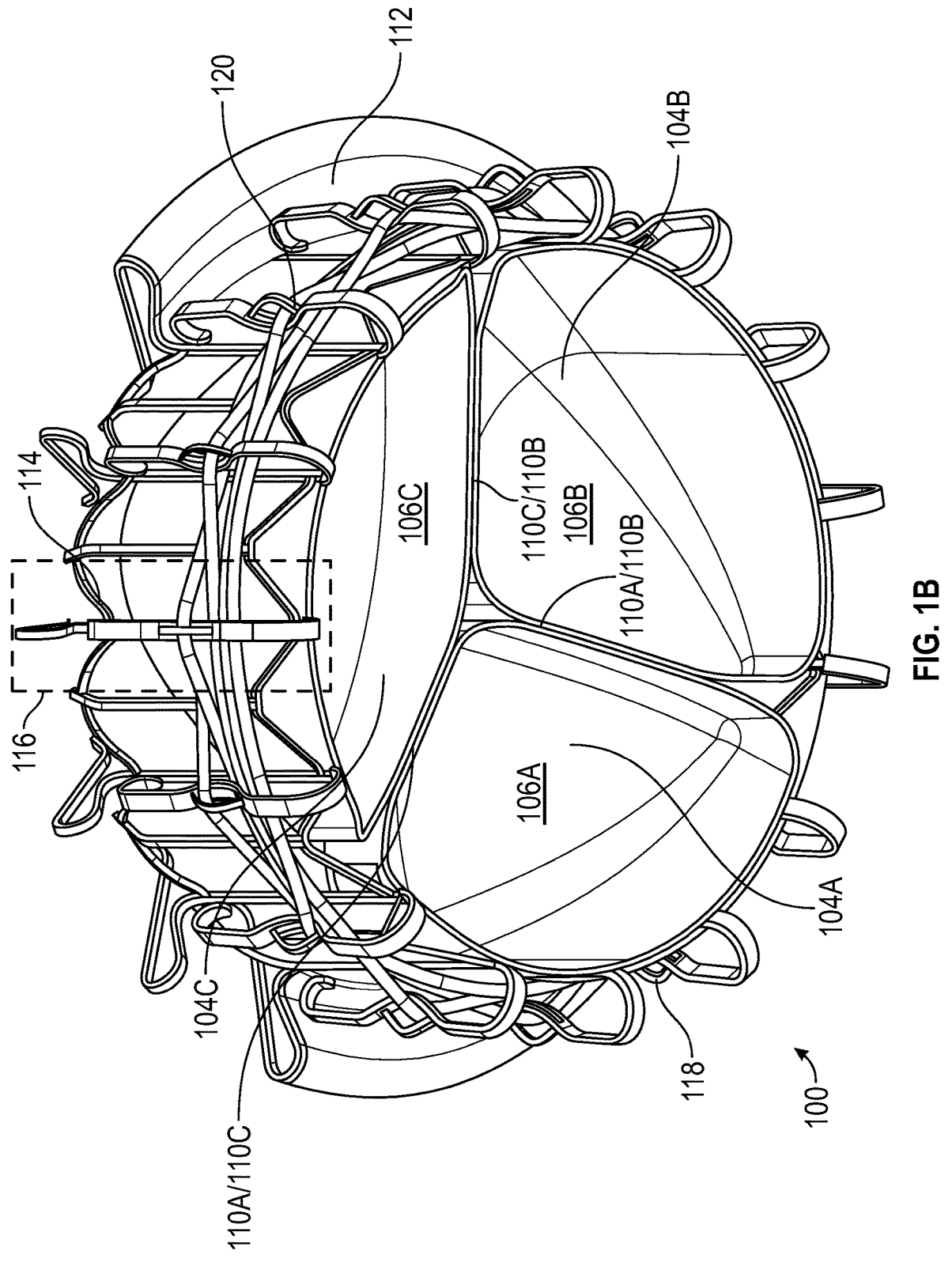
Figure 1C:
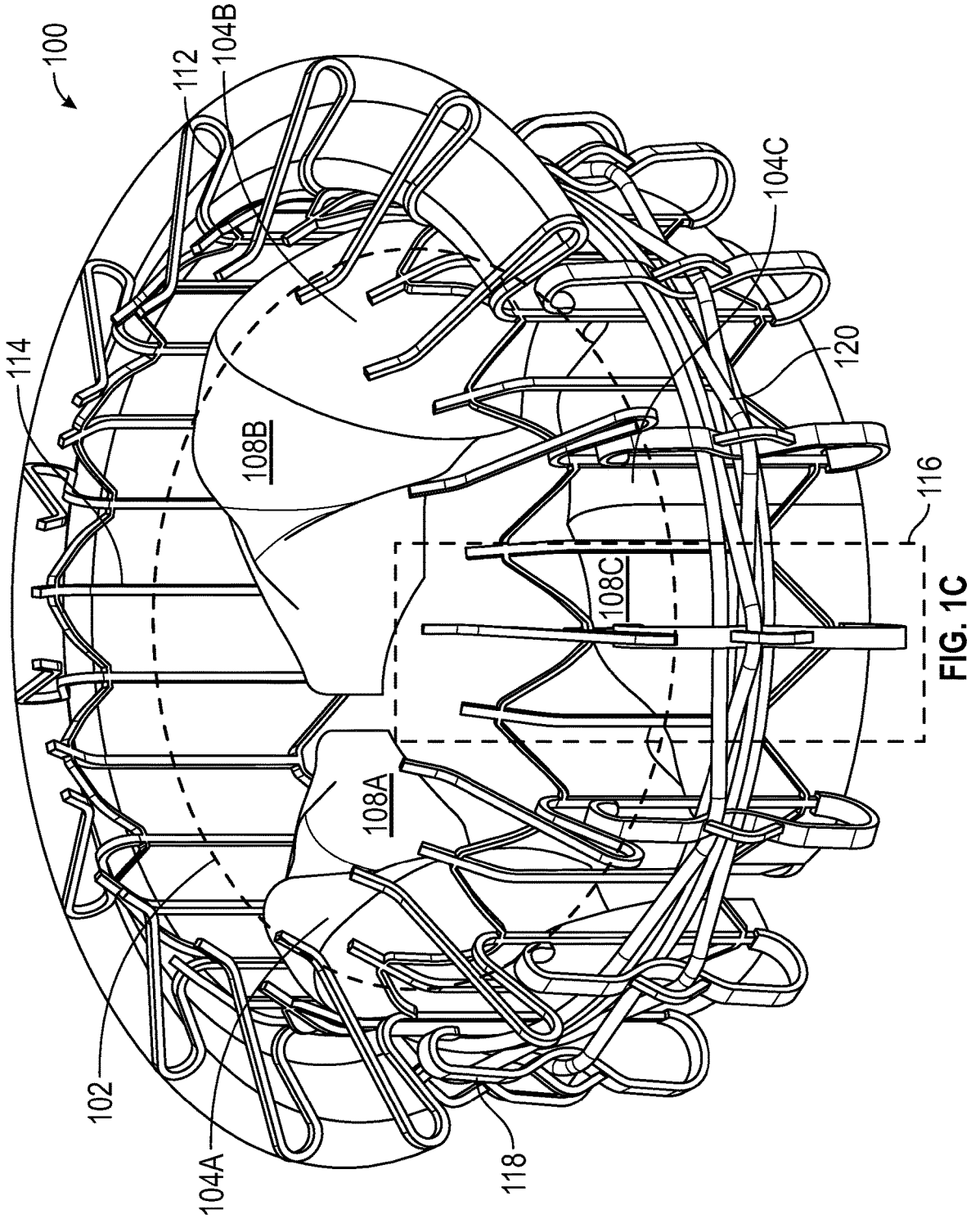

FIGS. 1A-1C illustrate an exemplary valve device 100. In some embodiments, the valve device 100 includes an opening 102 and leaflets 104A-104C (in the example of FIGS. 1A-1C, valve device 100 includes three leaflets 104A-104C, but those skilled in the art will recognize valve device 100 can include more or less than three leaflets). The leaflets may include downstream surfaces 106A-106C and upstream surfaces 108A-108C. Further configurations, variations, and embodiments of the device are provided in the Appendix.

In some embodiments, the leaflets' upstream surfaces 108A-108C collectively occlude the opening 102 when the leaflets 104A-104C are in a first configuration (for example, the first configuration is the closed configuration illustrated in FIG. 1A). The opening 102 may be occluded such that no fluid (e.g., no blood pumped from a heart muscle or an amount that meets or an amount that is less than the reverse flow requirement per ISO 5840-3) may flow between through the opening 102 (e.g., during reverse flow). In some examples, the opening 102 may be occluded when the interfacing surfaces 110A-110C of each leaflet are in contact with interfacing surfaces of another leaflet, creating a seal, such that no fluid may flow through the interfacing surfaces. This occlusion by the leaflets may be known as coaptation and the interfacing surfaces 110A-110C may be termed coaptation surfaces. During reverse flow, some of the reverse flow may be caught at the downstream surface (e.g., pockets), thus inflating them, like a parachute.

In some embodiments, the device 100 is in a first configuration in response to no force or a force from the downstream side to the upstream side, and the device 100 is in a second configuration in response to a force from the upstream side to the downstream side (e.g., the opening does not occlude). For example, the first configuration is a closed configuration, as illustrated in FIG. 1A or 1B, and the second configuration is an open configuration, as illustrated in FIG. 1C. The valve device 100 may be in a closed configuration when the opening 102 is occluded and no fluid (e.g., no blood pumped from a heart muscle or an amount that meets or an amount that is less than the reverse flow requirement per ISO 5840-3) may flow across the opening 102. The direction of the blood flow and the force may cause the leaflets 104A-104C to occlude the opening 102. When the opening 102 is occluded, blood flowing in this direction may be trapped in the downstream surfaces 106A-106C (e.g., the blood cannot continue flowing in this direction). The valve device 100 may be in an open configuration when the opening 102 is not occluded and fluid (e.g., blood pumped from the upstream to downstream direction) may flow across the opening.

In some embodiments, the leaflets return toward a manufactured or an inflated shape in response to an increase of the blood being trapped. For example, analogous to air in a parachute, as pressure against the downstream surface (e.g., inside the pocket) increases, the leaflet inflates until it reaches its full, manufactured, or inflated shape. The pressure against the downstream surface causing the leaflet to reach its full, manufactured, or inflated shape may be equal to the maximum pressure required by ISO 5840 for the valve in a deployed location (e.g., 165 mmHg for Aortic, 210 mmHg for Mitral, 42 mmHg for Pulmonary, 59 mmHg for Tricuspid). The leaflets may be deformable (e.g., in a way that allows blood to flow when the device is in an open configuration, in a way that allows the collapsed device to fit in a catheter) under applied pressure from the upstream side. In some embodiments, the leaflet may return to a manufactured or an inflated shape upon an increase in pressure on the downstream side. For example, when the valve device is in an open configuration, a first force, caused by blood flow from the upstream to the downstream direction, deforms one or more leaflets (e.g., the blood pushes the thin-film leaflet, deforms the manufactured shape of the leaflet, and the deformation opens up an area for blood to flow across the opening). Subsequently, blood flow from the upstream to the downstream direction may cease, and a second force, caused by blood flow from the downstream to the upstream direction or a force from the downstream to upstream direction may cause the valve device to be in a closed configuration. In the closed configuration, the leaflet may return to a manufactured or an inflated shaped (e.g., a leaflet shape described with respect to FIGS. 2A-2C, a leaflet shape without a force acting on the leaflet). When the valve device is in a closed configuration, blood flow from the downstream to the upstream direction may be trapped on the downstream surface and the leaflet maintains its manufactured or inflated shape.

In some embodiments, flow is created by a heart muscle and pumps blood in directions perpendicular to the opening of the device. The heart muscle may be a muscle from the right atrium, the right ventricle, the left atrium, or the left ventricle. When valve device 100 is used in a tricuspid location (e.g., the valve is anchored to native tricuspid leaflets, the valve is anchored to tricuspid valve annulus), forward flow may be flow of blood pumped from the right atrium to the right ventricle during ventricular diastole, and reverse flow may be flow of blood pumped from the right ventricle to the right atrium during ventricular systole. In these examples, when the valve device is attached to the native tricuspid valve (e.g., the valve is anchored to native tricuspid leaflets, the valve is anchored to tricuspid valve annulus), the upstream surface may be facing toward the right atrium, and the downstream surface may be facing the right ventricle. Blood pumped from the right ventricle toward the right atrium during systole (e.g., reverse flow) may cause a force in a direction from the downstream surface to the upstream surface. Blood pumped from the right atrium to the right ventricle during diastole may cause a force in a direction from the upstream surface to the downstream surface. In the tricuspid embodiment, a full opening may have a diameter in a range of 30-60 mm.

When the valve device is used in a mitral valve location (e.g., the valve is anchored to native mitral leaflets, the valve is anchored to mitral valve annulus), forward flow may be flow of blood pumped from the left atrium to the left ventricle during ventricular diastole, and reverse flow may be flow of blood pumped from the left ventricle to the left atrium during ventricular systole. In these examples, when the valve device is attached to the native mitral valve (e.g., the valve is anchored to native mitral leaflets, the valve is anchored to mitral valve annulus), the upstream surface may be facing toward the left atrium, and the downstream surface may be facing the left ventricle. Blood pumped from the left ventricle to the left atrium during diastole may cause a force in a direction from the downstream surface to the upstream surface. Blood pumped from the left atrium to the left ventricle during diastole may cause a force in a direction from the upstream surface to the downstream surface. The direction of the blood flow and the force may cause the leaflets be in an open configuration, when blood flows across the opening. In the mitral valve embodiment, a full opening may have a dimension in a range of 20-50 mm (e.g., diameter, septal-lateral dimension of a "D" shaped opening).

When the valve device is used in an aortic valve location, forward flow may be flow of blood pumped from the left ventricle to the aorta during ventricular systole, and reverse flow may be flow of blood from the aorta to the left ventricle during ventricular diastole. In these examples, when the valve device is attached to the native aortic valve, the upstream surface may be facing toward the left ventricle, and the downstream surface may be facing the aorta. In these embodiments, a full opening may have a diameter in a range of 20-30 mm.

When the valve device is used in a pulmonic valve location, forward flow may be flow of blood pumped from the right ventricle to the pulmonary artery during ventricular systole, and reverse flow may be flow of blood from the pulmonary artery to the right ventricle during ventricular diastole. In these examples, when valve device 100 is attached to the native pulmonic valve, the upstream surface may be facing toward the right ventricle, and the downstream surface may be facing the pulmonary artery. In these embodiments, a full opening may have a diameter in a range of 20-40 mm.

Returning to FIG. 1A, in some embodiments, leaflets 104A, 104B, and 104C are three-dimensional leaflets. In some embodiments, leaflets 104A, 104B, and 104C are three-dimensional thin-film leaflets. As used herein, a three-dimensional leaflet may comprise a shape having dimensions of height, length, and width, wherein the film thickness is smaller than (e.g., less than 0.01 times) any of the height, length, and width dimension. A three-dimensional thin-film leaflet may be manufactured without involving additional steps to join edges of a flat thin-film or otherwise support the shape. As illustrated, each leaflet may be in the shape of a dome. Exemplary dimensions of the leaflets 104A-104C will be described in more detail with respect to FIGS. 2A-2C. In some examples (e.g., in the aortic location, in the pulmonary location, in locations where the native valve does not include chordae), the leaflets may also be called a cusp. The disclosed manufacturing techniques may allow the described three-dimensional geometry of the thin-film leaflet to be formed.

Traditional leaflets are formed initially from flat and planar material (e.g., pericardial valves). A third dimension (e.g., beyond the thickness of the material) may be formed by sewing or welding that brings multiple planar edges together or by including support from an external frame. In contrast, the shape of the disclosed three-dimensional leaflet may be manufactured when using film deposition. Thus, for example, the "parachute," "balloon," or "dome" shape of the disclosed three-dimensional leaflet may be formed without any joints or additional processes. These additional processes may be sewing or welding that brings multiple planar edges of a two-dimensional thin-film together or by including support from an external frame. The additional processes may add to the size, cost, and manufacturing complexity of a valve device (e.g., existing mitral, aortic, or pulmonic valve designs).

As an exemplary advantage, the three-dimensional thin-film leaflet may be thinner than that of animal tissue or polymer or that formed by the additional sewing or welding process. A valve device including thinner leaflets may be easier to deploy through a catheter, especially for a larger valve device (e.g., a valve device for the tricuspid valve). Thus, the size of the valve device may be reduced using embodiments herein. Delivering larger devices may increase bleeding complications, cause damage to the vascular structures, or may not be possible. The thinner material may allow the valve to open and occlude more easily. Furthermore, thin-films can be biocompatible materials that have a longer lifetime (e.g., longer than 10 years), compared to existing mitral, aortic, or mitral valve designs, after the valve device is implanted into the body. A material may be biocompatible if it is suitable for long-term implantation in the body. Compared to a sewn valve design, the three-dimensional thin-film leaflet may be more cost-effective and may take less time to manufacture. Thin-film technology may eliminate manufacturing steps, potentially resulting in significant cost savings. Further, thin-film production may be automated and/or easily scaled for bulk production. Compared to a thin-film fabricated from a flat design, a three-dimensional thin-film leaflet may have superior mechanical properties (e.g., better structural integrity, stops reverse flows more efficiently (e.g., minimizing reverse flow across the opening while the valve is occluding)). The valve device, using embodiments herein, forms each valve leaflet pocket (e.g., downstream surface of a leaflet) from a single piece forming a net shape. Therefore, heat shaping or cold working may not be required to form the final device. The material properties of the three-dimensional leaflet would result in better fatigue life, durability, and strength.

Although the valve device 100 is described with respect to the tricuspid, mitral, aortic, or pulmonic valve, it is understood that the valve device 100 may anchor to other parts of the body without departing from the scope of the disclosure.

With reference again to FIGS. 1A-1C, each leaflet may comprise an interfacing surface 110A-110C that, while the leaflets occlude the opening, contacts an adjacent leaflet's interfacing surface. For example, the valve device is in a closed configuration when adjacent leaflets contact each others' interfacing surfaces and no fluid (e.g., blood) flow across the device's opening through the interfacing surfaces (e.g., the contacts between the interfacing surfaces seal the opening). In some embodiments, the interfacing surface has a height of 2-10 mm. As an exemplary advantage, the interfacing surface height, resulting from the leaflet's three-dimension geometry, allows a tighter seal, compared to seals formed with a smaller interfacing surface area, during reverse flow and better structural integrity when a force caused by the reverse flow acts on the downstream surfaces of the leaflets.

Valve device 100 may include frame 114. In some embodiments, the frame 114 defines the opening 102, and each leaflet 104 is attached to the frame 114. In some examples, the frame 114 is a stent frame. The frame may be created by laser cutting. Although the frame 114 is shown with leaflets 104 attached, it is understood that the frame 114 may be used without the leaflets attached. For example, frame 114 could be used with other occlusion devices in place of leaflets 104A-C. Further configurations, variations, and embodiments of the frame are provided in the Appendix.

The leaflets may be welded, sewn, clamped, or glued to the frame. A second layer of vapor deposition may create a weld at the nano scale. A pocket or hole within the film may be created by using etching techniques to remove material. A post from the stent frame may be inserted into the pocket or hole, and the leaflet may be bonded to the frame. As an exemplary advantage, the methods of leaflet attachments to the frame may prevent para-valvular leak (PVL) (e.g., blood leakage around the device, blood leakage not across the opening of the device). The frame may include guides or features that cause the leaflet to collapse in a particular way when the valve device is collapsed (e.g., in a catheter).

As illustrated, the frame may include cells 116. In some embodiments, the frame includes nine cells. In some embodiments, the frame includes twelve cells. In some embodiments, the frame includes fifteen cells. The number of cells may allow a cord, described in more detail below, to be in a triangular shape when connected to the frame. Although specific numbers of cells are stated, it is understood that the frame may include any number of cells. It is also understood that the cells of the frame may have different sizes. The cells may be linked together into a cylindrical shape to form a collapsible frame. A cell may include an extension (not shown) in a direction toward the downstream surface, creating a lower portion. The leaflet may be attached to a portion of the cell above the lower portion of the cell. As an exemplary advantage, attaching the leaflets as described may allow collapse of the stent frame without creating any relative vertical movement of the connected points on the film. The cells may be collapsible (e.g., in a shape that accommodates the device in a catheter) in response to a force (e.g., when fitted into a catheter) and return to its manufactured shape when no force is acted on the cell. The cells may be designed such that the frame returns to its manufactured or resting shape due to spring force from the cells. Further configurations, variations, and embodiments of the cell are provided in the Appendix.

In some embodiments, the frame is a stent frame having anchoring prongs 118 to maintain the device at a native valve (e.g., tricuspid valve, mitral valve) location. The anchoring prongs may rest (e.g., before the device is anchored to the native leaflets) at an angle between 0 and 90 degrees (e.g., 45 degrees) relative to the stent frame, wherein the angle of 0 is defined by an axis from a downstream to an upstream direction along the stent frame. The anchoring prongs may be attached to some of the cells 116 of the frame 114. As an exemplary advantage, at a resting angle between 15 and 60 degrees, tightening of a cord connecting an anchoring prong naturally pulls the anchoring prong inwards, toward the center of the frame, and anchoring the valve device to the native leaflet, as described below.

In some embodiments, the valve device includes three prongs. In some embodiments, the device includes six anchoring prongs. In some embodiments, the device includes nine anchoring prongs. In some embodiments, the device includes twelve anchoring prongs. In some embodiments, the device includes fifteen anchoring prongs. In some embodiments, the device includes 24 anchoring prongs. In some embodiments, the device includes 30 anchoring prongs. It is understood that the valve device may include other numbers of prongs. In some embodiments, as illustrated, the anchoring prongs 118 are equally-spaced along a circumference of the frame. In some embodiments, the anchoring prongs have different spacing between adjacent prongs.

In some embodiments, the stent frame further includes a cord 120 connecting the anchoring prongs, where the cord can tighten and pull the anchoring prongs toward the frame as the frame expands. For example, the valve device includes fifteen cells, each having an anchoring prong attached, and five cords, each cord connected to three anchoring prongs. As another example, the cord is connected to three anchoring prongs. Further configurations, variations, and embodiments of the cord are provided in the Appendix.

There may be two or more sets of prongs connected by multiple cords. The device 100 may comprise a second cord connected to three second anchoring prongs, each of the second anchoring prongs may be at a position adjacent on the frame to a first anchoring prong. For example, in a device with six anchoring prongs A-F, in order around the circumference of the frame, there may be three cords connecting A-D, B-E, and C-F, or two cords connecting A-C-E and B-D-F. In these exemplary configurations, the cord may traverse the opening of the device or may be wrapped around the outer circumference of the stent frame. In some examples, one cord may be connecting adjacent prongs (e.g., A-B, B-C, etc.).

In some embodiments, the cord comprises at least one of a wire rope of one of Nitinol, a wire rope of a non-Nitinol biocompatible alloy, a solid or multi-filar cord of a PTFE, a solid or multi-filar Kevlar cord, and a non-PTFE and a no-Kevlar solid or multi-filar cord.

In some embodiments, the anchoring prongs are in a pinching position upon contact with an underside of native leaflets. For example, during delivery, when the valve device reaches a native leaflet location, the valve device may be partially released from the catheter. The collapsed frame (described in more detail below) of the valve device may expand (e.g., in response to an input). The frame may expand when it is at least partially released from the catheter. In some embodiments, the proximal end of the frame or the atrial skirt prongs may still be in the catheter when the device is partially released. In some embodiments, an input causing the valve device to expand or partially expand may be an action of the operator extending the device from the catheter or retracting the sheath of the catheter while holding the valve steady. This action may be taken prior to positioning the prong tips against the underside of the leaflets.

In some embodiments, the anchoring prongs are configured to draw a valve annulus toward a center of the opening. For example, after an anchoring prong is placed against the ventricular side of the valve annulus, further expansion of the stent frame and the associated tightening of the anchoring cord may cause the tips of the anchoring prongs to be drawn inward, which may cause a valve annulus to be pulled toward a center of the opening of the device, reducing a valve annulus circumference or diameter. By being configured to draw the valve annulus toward a center of the opening of the device, the anchoring prongs may advantageously achieve effects of valve annuloplasty.

The expansion of the frame may cause the cord to tighten, pull tips of the anchoring prongs toward the native leaflet, and pull the tips of the anchoring prongs toward the stent frame, such that the native leaflets may become trapped between either the anchoring prong and/or the anchor cord and the stent frame. Further expansion of the frame may pinch the native valve (e.g., tricuspid, mitral leaflets) between the frame and the anchoring prongs, anchoring the valve device to the native leaflets. The cord may allow the prongs to reach their full radial extension (maximum radius of a circumference formed by the prongs), while a portion of the frame remains crimped within the delivery catheter. The cord and frame together may limit prong radial extension to the full radial extension value or less as the frame is expanded to its full diameter. As an exemplary advantage, because the tricuspid annulus has a thin fibrous structure and is less likely to calcify, the described anchoring mechanism may be more effective, compared to anchoring with an outward radial force.

In some embodiments, the valve device further comprises cord attachment points (not shown) between adjacent anchoring prongs of a set of anchoring prongs to secure the cord. In some embodiments, the cord attachment points are parts of the frame. In some embodiments, the cord attachment points are attached to the frame.

Although specific configurations of anchoring prongs and cords are expressively described, it is understood that the disclosed valve device may include different configurations of anchoring prongs and cords.

In some embodiments, the frame is cylindrical and a portion of the leaflet attached matches a contour of the frame (e.g., the portion is partially cylindrical). In some examples, as illustrated, the interfacing surface 110 is oriented in a direction parallel to the valve device's central axis (e.g., an axis perpendicular to a plane of the opening and passing through the center of the opening).

In some embodiments, a portion of the leaflet attaches to the frame, and the portion comprises non-uniform thickness. As an exemplary advantage, stress concentrations may be reduced at locations where the leaflet is attached to the frame.

In some embodiments, the valve device 100 includes a frame 114 and a skirt 112 attached to the frame and outside the opening to stop blood (e.g., pumped by the heart muscle) in a direction from the downstream surface to the upstream surface outside the opening. In some embodiments, the skirt may stop blood from the upstream surface to the downstream surface outside the opening. For clarity, part of the skirt 112 is not shown; it is understood that the skirt 112 may wrap around the frame of the described valve device. In some embodiments, the skirt is an atrial skirt located on an edge of the frame. The skirt may be part of the frame or made from a film or fabric, which may be knit or woven PET fabric, expanded PTFE (EPTFE), thin-film Nitinol, or polymer film. The fabrics or films may have porosity of a size designed to encourage in-growth or endothelization to further anchor the device and prevent PVL. For example, when the device is attached to the native leaflets, a part of the frame rests on the atrial side of the native leaflets, along with the atrial skirt, creating a seal that prevents PVL. Further configurations, variations, and embodiments of the skirt are provided in the Appendix.

Although the exemplary valve device 100 consists of three leaflets, it is understood that the valve device 100 may include other numbers of leaflets without departing from the scope of the disclosure. For example, the valve device 100 may consist of one leaflet, which is configured to perform functionalities described herein. The leaflet may be a single dome. Some portion of the circumference may be attached to the frame, and the remaining portion may be free to move. Forward flow (e.g., atrial pressure) would collapse this dome downward, and reverse flow (e.g., ventricular pressure) would cause it to inflate and close. To prevent leakage, a fixed film on the circumference of the frame may provide a second coaptation surface, allowing the leaflet to seal against an outer rim. When the device is in a closed configuration, the one leaflet may prevent flow across the opening of the device.

As another example, the valve device 100 may consist of two leaflets, which are configured to perform functionalities described herein. As yet another example, the valve device 100 may consist of four or more leaflets, which are configured to perform functionalities described herein.

Although the leaflets are illustrated as having approximately same sizes, it is understood that the leaflets may have different sizes without departing from the scope of the disclosure. For example, the valve device 100 may include leaflets of different sizes and the leaflets may be configured to perform functionalities described herein.

Figure 2A:
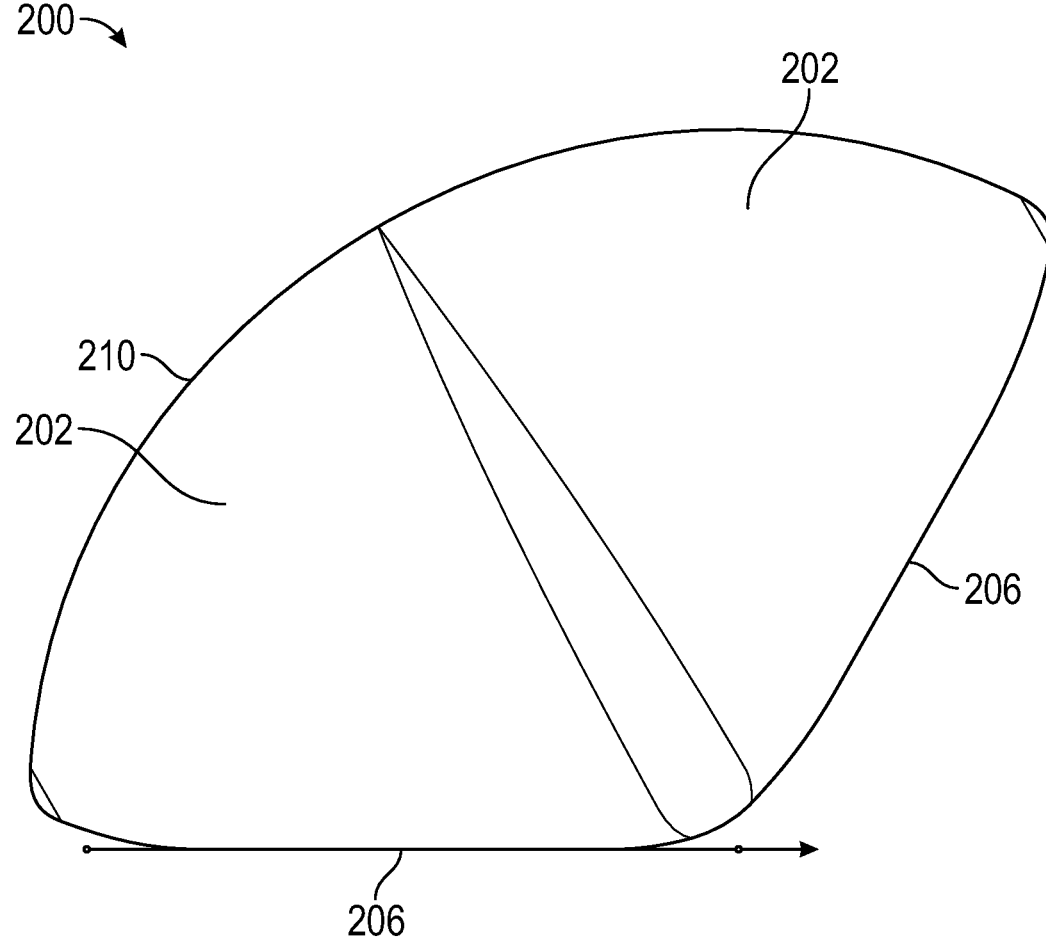
FIGS. 2A-2F illustrate an exemplary leaflet.
Figure 2B:
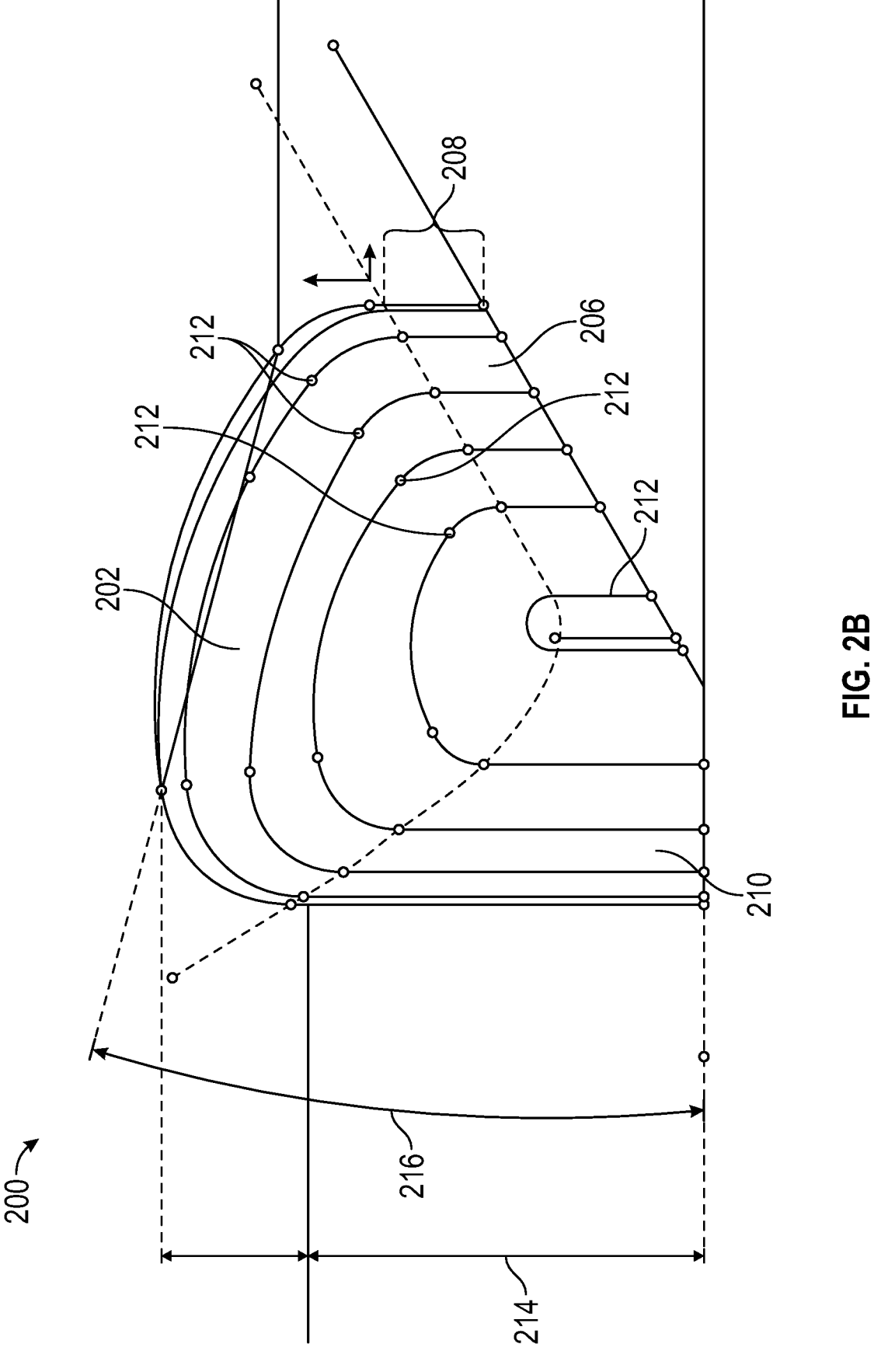
Figure 2C:
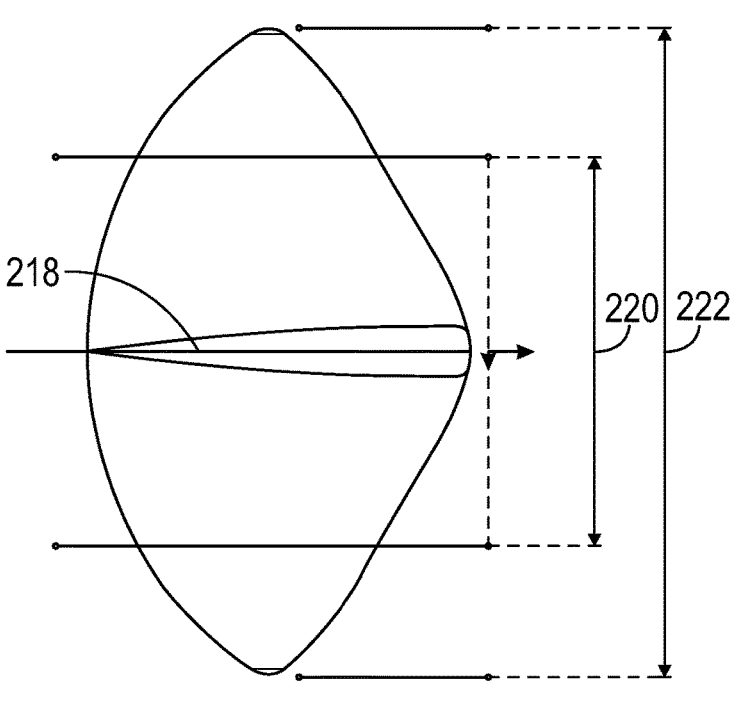
Figure 2D:
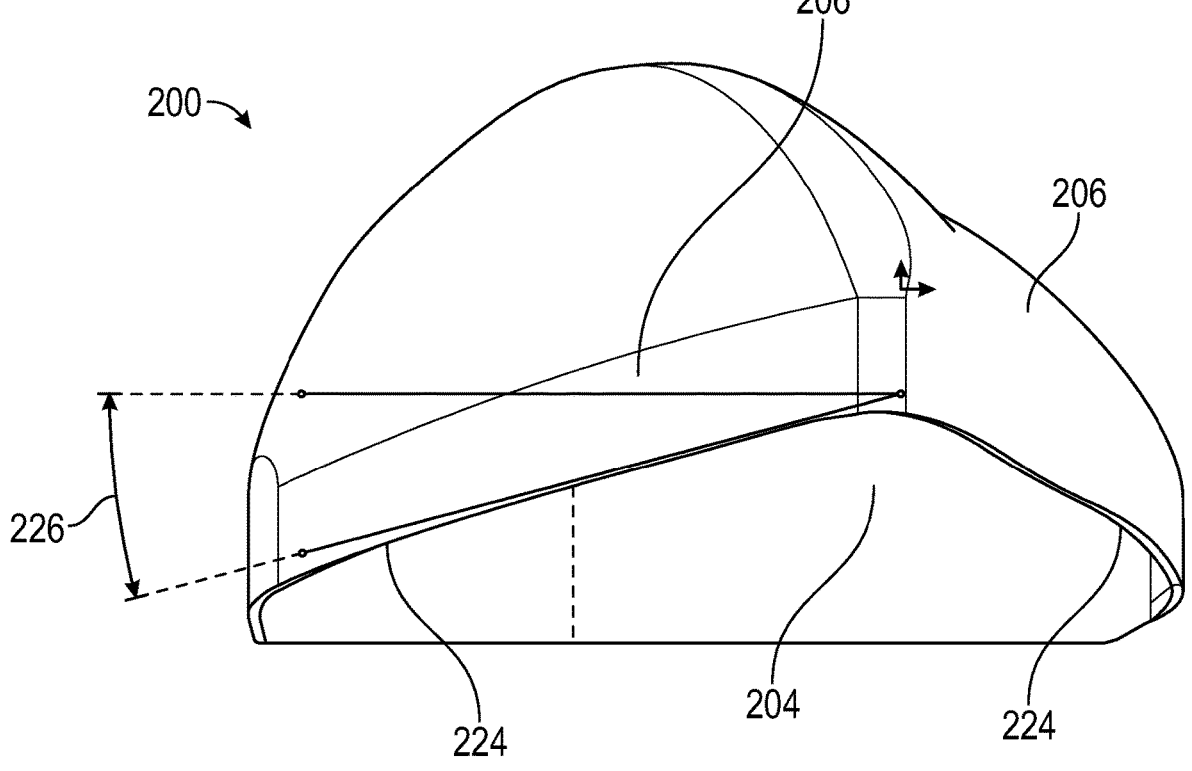

FIGS. 2A-2C illustrate an exemplary leaflet 200. The leaflet 200 may be substantially similar to one of leaflets 104A-104C. FIG. 2A is a top view of the leaflet 200. FIG. 2B is a view of the leaflet from a side of the leaflet toward an interfacing surface and an outer cylindrical surface. FIG. 2C is another top view of the leaflet 200. FIG. 2D is a view of the leaflet toward a downstream surface of the leaflet. In some embodiments, the leaflet 200 is part of a deployed valve device and the valve device is in a closed configuration.

The leaflet 200 may include an upstream surface 202, a downstream surface 204, and interfacing surfaces 206. In some embodiments, the leaflet 200 is a three-dimensional thin-film leaflet. In some embodiments, the leaflet 200 is a three-dimensional leaflet including material other than thin-film. As illustrated, the leaflets may be in the shape of a dome. In some embodiments, the leaflet may be in a shape of a cusp. In some embodiments, the interfacing surfaces 206 have a height 208 of 2-10 mm. In some embodiments, the thin-film leaflet includes an outer cylindrical surface 210.

As illustrated in FIG. 2B, the upstream surface 202 of the leaflet comprises a dome portion 232, which will be described in more detail below. For example, the upstream surface 202 may be convex. As an exemplary advantage, the convex upstream surface may provide a more uniform tension within the leaflet when the leaflet is inflated (e.g., the valve is in an occluded configuration). As an exemplary advantage, a dome portion that tapers in a direction toward an adjacent leaflet from the upstream to the downstream surface may cause pressure to be more focused and causes the leaflet to be less-likely to flail when the valve is occluding, while minimizing stasis and thrombus and allowing the leaflets to more fully occlude the opening.

The three-dimensional geometry of the leaflet 200 may be described using a set of profiles 212 spanning a portion of the shape of the leaflet. A profile may be understood as a shape of a cross-section of the leaflet in a midplane 218 or any plane parallel to the midplane 218 when the valve device is deployed and the valve device in a closed configuration under pressure (e.g., equal to the maximum pressure required by ISO 5840). The midplane 218 may be understood as a plane passing through the opening's central axis and midway along depth 222 of the leaflet. For example, the set of profiles 212 defines the shape of a symmetrical half of the leaflet. It is understood that the profiles 212 are included in the Figure for illustrative purposes.

The dimensions of each profile 212 includes an interfacing surface height 208, an outer cylindrical surface height 214, and a profile slope angle 216. In some embodiments, the interfacing surface height 208 of a profile is the dimension of a portion of the profile that is part of the interfacing surface 206. As discussed, the interfacing surface height may be 2-10 mm. Although the interfacing surface is illustrated as being vertical, it is understood that the interfacing surface may be at an angle between −10 and 10 degrees relative to the valve's central axis and/or may not be straight or linear.

In some embodiments, the outer cylindrical height 214 of a profile is the dimension of a portion of the profile that is part of the outer cylindrical surface 210. In some embodiments, the outer height 214 is 3-25 mm. Although the outer cylindrical surface is illustrated as being vertical, it is understood that the outer cylindrical surface may be at an angle between −10 and 10 degrees relative to the valve's central axis and/or may not be straight or linear.

In some embodiments, the profile slope angle 216 is defined by an angle between a plane perpendicular to the valve's central axis and a line between the 10% the 90% profile width points. The 10% profile width point (e.g., point 228) is the point of profile 212 that corresponds to 10% of the profile's width from the outer cylindrical surface side. The 90% profile width point (e.g., point 230) is the point of the profile 212 that corresponds to 90% of the profile's width from the outer cylindrical surface side. The width of profile 212 is defined by the span from a point on the profile closest to a plane passing through the valve's central axis and perpendicular to the profile plane (e.g., an end location on an interfacing surface portion of the profile) to the point on the profile farthest from that plane (e.g., an end location on an outer cylindrical surface portion of the profile). A positive profile slope angle 216 may be defined by a position of the 10% profile width point being in more upstream direction with respect to the valve's central axis than the position of the 90% profile width point. In some embodiments, the profile slope angle 216 is −45 to 45 degrees. For example, leaflets may include profile slopes between −5 and 15 degrees. In some embodiments, the leaflet includes profile slopes between 0 and 15 degrees.

For each profile 212, the width between the interfacing surface 206 and the outer cylindrical surface 210 may be determined by the leaflet configuration of the valve device 100. For example, if the valve device 100 has three leaflets having the same shape, then the interfacing surfaces 206 of a leaflet forms a 120 degree angle. Based on this angle and the size of opening, the width of each of the profiles 212 can be determined.

The leaflet 200 may be additionally defined by an average slope. The average slope of the leaflet 200 may be defined by as the average of the profile slopes within the middle 60% of the leaflet depth 222, which may be measured in a direction perpendicular to the midplane 218. The average slope of the leaflet 200 may define the dome portion of the leaflet. The average slope may be calculated using the following formula:

$$\frac{\int_{0.2D}^{0.8D} S(x)\,dx}{0.6D} \tag{1}$$

Wherein S(x) may be understood as the function of the slope of the profile at location x along the depth 222, x=0 may be understood as an end of depth 222, and D may be understood as the dimension of the depth 222 of the leaflet. Although the middle 60% of the depth is used in this example, it is understood that other middle sections (e.g., middle 40% of the depth, middle 80% of the depth) of the depth may be used to calculate the average slope to associate with the dome portion of the leaflet. In some embodiments, the average slope of the leaflet 200 is between 0 and 45 degrees. For example, leaflets may include average profile slopes between 10 and 15 degrees. In some embodiments, the leaflet has an average slope of 12 degrees.

As an exemplary advantage of the exemplary leaflet geometries having profiles 212 that include the exemplary profile slope angles, this leaflet design may resist flailing during reverse flow by directing forces at more focused areas of the leaflet. For example, a volume may exist above the upstream surface of the leaflet, located between the domed surface of the leaflet and the wall of the upstream chamber of the heart, and radially outward from the valve axis. In the tricuspid location, the walls would be walls of the right atrium. In the mitral location, the walls would be walls of the left atrium. In the aortic position, the walls would be walls of the left ventricle. In the pulmonary position, the walls would be the walls of the right ventricle. During the phase when the valve closes (e.g., systole for a tricuspid or mitral location; diastole for an aortic or pulmonary location), this volume may be at a lower pressure, and the pressure imbalance may cause the leaflets to move outward in an opening direction, rather than inflating and creating coaptation or sealing with other leaflets, causing the leaflets to invert and become "flail." However, in a device having leaflets with a profile slope angle as disclosed, this volume within the upstream chamber of the heart is smaller. The smaller volume causes the net forces to push the leaflet toward the center axis (e.g., occluding the opening) rather than away from it, thus causing the leaflet to create a seal against its counterparts rather than invert and become "flail".

In some examples, the downstream surface is a domed surface along one of radial and lateral directions to reduce at least one of stress and stasis. For example, the domed surface is described with respect to FIGS. 2A-2C.

As another exemplary advantage, the geometry of the leaflet may be beneficial in preventing stasis within the downstream surfaces of the leaflet, especially near an intersection of an interfacing surface 206 with a cylindrical surface 210 interfacing the frame. To prevent stasis and thrombus, the geometrical transitions (e.g., edges, corners) may be round and having a larger corresponding radii (e.g., a radius of transition above the outer cylindrical surface being greater than 1 mm, a radius of transition above the interfacing surface portion being radius greater than 1 mm); blood would be less likely to get caught at these transitions during reverse flow while the mechanical strength (e.g., fatigue life) of the leaflet can be retained. The larger corresponding radii may also allow the valve to open and occlude more easily and provide a more uniform tension within the leaflet when the leaflet is inflated (e.g., the valve is in a closed configuration). In some embodiments, the corresponding radii may vary along an interface between the interfacing surface and the downstream surface.

The leaflet may include a rim on an edge of the interfacing surface in the forward flow direction. The portion of the rim nearest the central axis of the valve may be in a more upstream position; the portion of the rim extending toward the outer cylindrical surface of the valve may extend toward the downstream direction. For example, the lower portion of the interfacing surface 206 includes a rim 224. In some embodiments, the edge of the rim forms an angle 226 with a plane of the opening 102. The angle 226 may be 0-60 degrees. For example, the angle 226 may be fifteen degrees.

As an exemplary advantage, when the valve is pressurized (e.g., when the upstream and downstream surfaces are in tension), a tensile force may be created within the interfacing surface 206 of the leaflet, thereby preventing leaflet flail.

More specifically, a rim sloping in this direction may allow the interfacing surface to induce a downward force on the upstream surface, thereby holding the leaflet in the proper location to prevent a "flail" leaflet when the valve is in a closed configuration (e.g., during systole for a valve in the mitral or tricuspid position, during diastole for a valve in the aortic or pulmonary position). Further, a portion of the interfacing surface may be solid or may be perforated to allow increased flow between the leaflets on the downstream side while the opening is occluded (e.g., from the interior pocket of one leaflet to its neighbor), thereby reducing stasis within the leaflet. For example, portions of the interfacing surface more proximate to the rim (e.g., more in the downstream direction) may be perforated and the remaining portions of the interfacing surface may be solid. This exemplary interfacing surface forms a better seal against a neighboring interfacing surface, and perforations more in the upstream direction may allow reverse flow because insufficient pressure may be created within the leaflet for it to close adequately.

As an exemplary advantage, reduction of stasis is desirable to prevent thrombus or clots from forming in the device; the clots may travel to the brain and cause a stroke (e.g., if the device is used in the mitral or aortic position) or to the lungs and cause a pulmonary embolism (e.g., if the device is used in the tricuspid or pulmonic position). When valve device is in a closed position, blood may swirl in the heart chamber or interior of the leaflet pocket, passing through the perforations, resulting in better washout. When the valve is in an open position, the perforations may allow better washout by allowing blood to escape from within the collapsing leaflet, especially near the junction of the interfacing surfaces with the outer cylinder portion of the leaflet. The rim may have a lower edge that slopes downward from the center of the valve to the cylindrical surfaces. This shape may optimize direction of the forces in the.

In some embodiments, the leaflets comprise at least one of biocompatible alloy, polymer, and composite structure. In some embodiments, the leaflets are fabricated using vacuum deposition, PVD, or CVD. In some embodiments, the leaflets are formed by physical vapor deposition of at least one of an alloy and a polymer. In some embodiments, the alloy is superelastic Nitinol. In some embodiments, the polymer is Kevlar, Parylene, PTFE, or FEP. In some embodiments, the leaflets are formed by at least one of dipping, painting, and molding. As an exemplary advantage, due to the strength of the thin-film (e.g., the grain size in the films may be small, leading to excellent fatigue characteristics), a thinner material using vacuum deposition, PVD, or CVD may be used to reduce the size of the device and allow the device to be more suitable for delivery to native leaflets (e.g., tricuspid).

In some embodiments, a thickness along a surface of the leaflet is non-uniformed. For example, a thickness along an edge of a first portion of the leaflet is greater than a thickness of a second portion of the leaflet. As an exemplary advantage, stress concentrations on the leaflet may be reduced, and the leaflet may be more resistant to tearing and durable.

In some embodiments, the leaflets have a thickness of 5-250 μm. For example, the device is a tricuspid valve, and the thickness of the film may be 5-25 μm. As an exemplary advantage, the thinness of the thin-film (e.g., compared to a thickness in the order of 0.1-0.5 mm of other materials) allows a collapsible device comprising the thin-film to be transported more easily through a catheter.

In some embodiments, the leaflet includes stress relief features. For example, these stress relief features are stress relief cuts or stress relief holes. In some embodiments, the stress relief features are formed using at least one of laser cutting, photo-lithography, vapor deposition, hot-working, cold-working, photo-etching, and mechanical cutting. In some embodiments, the stress relief features are formed using a mold or substrate. In some embodiments, upstream surface may include ripples, which may aid stress reduction within the leaflet during occlusion. As an exemplary advantage, the features may be designed to reduce stress within the thin-film and thereby improve fatigue life and durability of the valve component.

In some embodiments, the interfacing surface comprises ridges and troughs. For example, the ridges and troughs may be parallel to a direction from the upstream surface to the downstream surface. As another example, a pattern of ridges and troughs may be oriented in a pattern that radiates from a central point near the top of the attachment of the leaflet to the frame; the trough or ridge nearest attachment point is vertical and the trough or ridge farthest from the attachment point may be at an angle between 0 and 60 degrees from the vertical axis. In some embodiments, the interfacing surface comprises dimples located periodically along the interfacing surface. In some embodiments, the interfacing surface comprises cuts. As an exemplary advantage, these features may reduce stress concentrations at locations where the leaflet is attached to the frame. Further configurations, variations, and embodiments of the leaflet are provided in the Appendix.

Although FIGS. 2A-2D illustrate a leaflet 200 as having specific features, it is understood that the Figure is not limiting and the leaflet 200 may include other features or not include the illustrated features without departing from the scope of the disclosure.

Figure 2E:
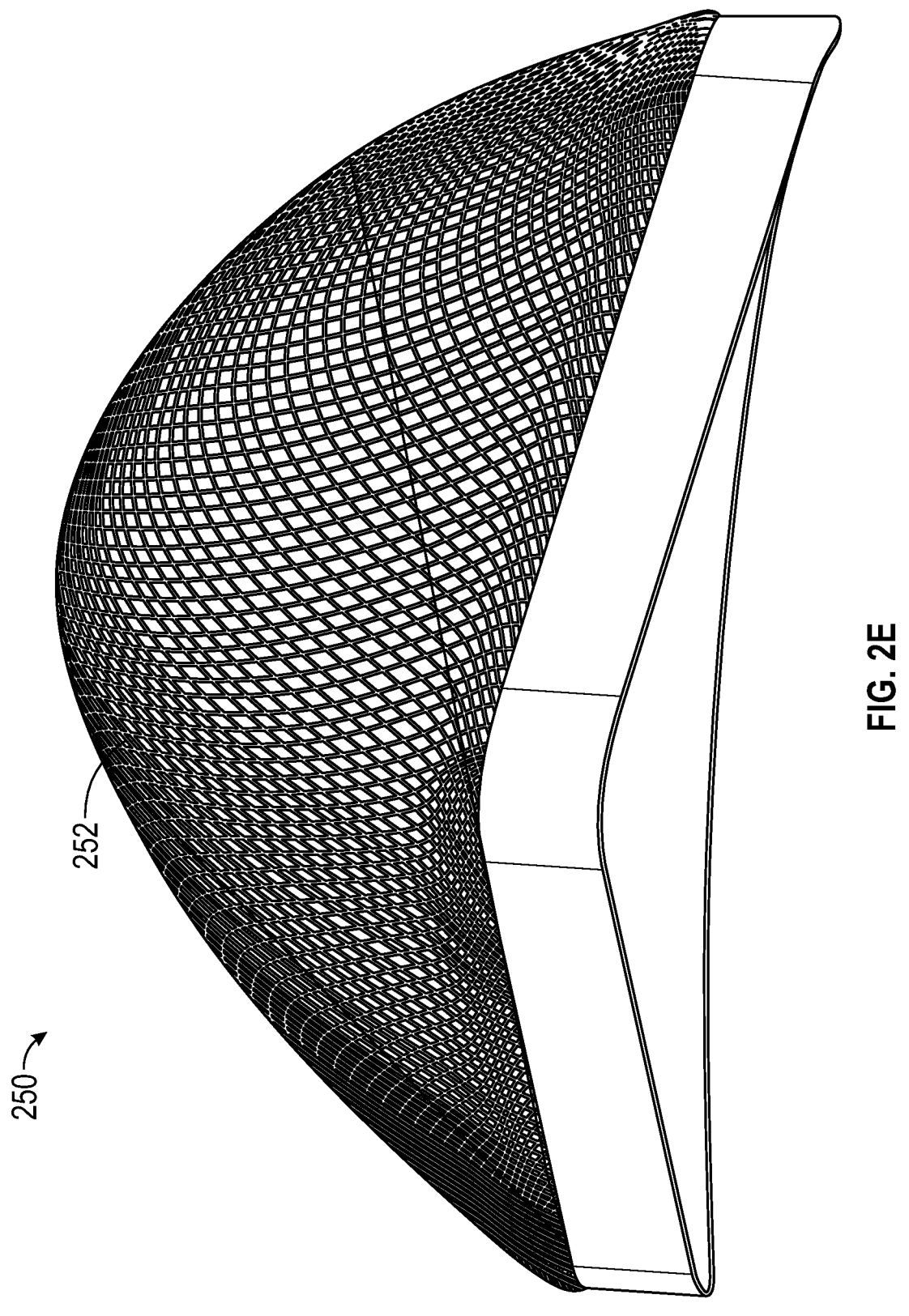

FIG. 2E illustrates an exemplary leaflet 250. In some embodiments, the leaflet 250 is leaflet 200 or one of leaflets 104A-104C. In some embodiments, the leaflet 250 includes texture 252. In some embodiments, the leaflet 250 is manufactured by a disclosed leaflet manufacturing process.

Figure 2F:
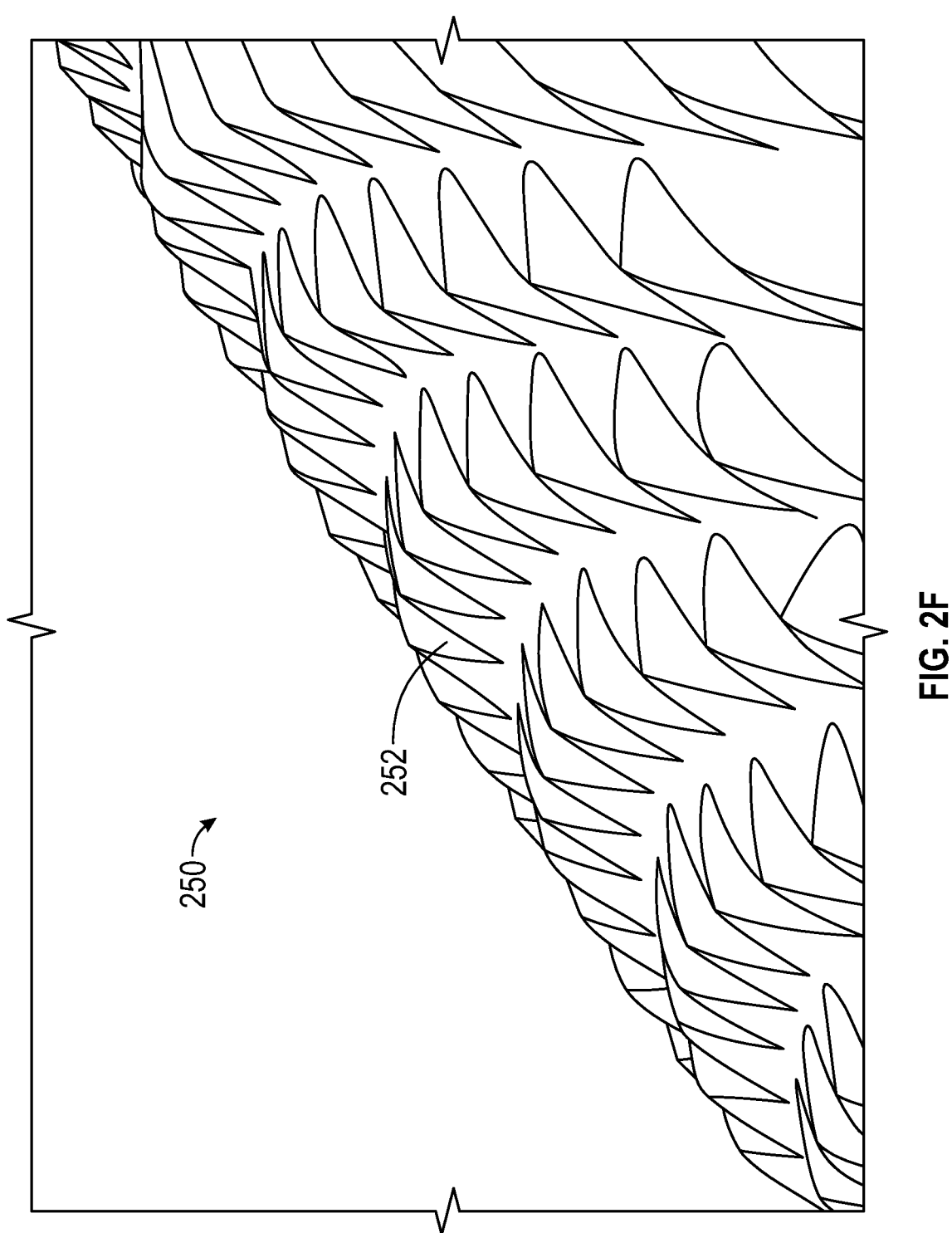

FIG. 2F illustrates a close-up view of the texture 252. In some embodiments, as illustrated, the texture 252 includes protrusions and trenches between the protrusions. For example, the protrusions may be organized in a grid pattern, and a part of a trench may be located between adjacent protrusions. The texture 252 may advantageously reduce stress in a corresponding region by allowing additional flexibility. For example, if a given fold in a non-textured leaflet would create excessive stress in a location on the leaflet, the addition of texture 252 may advantageously allow the stress to be relieved (e.g., the leaflet may fold at trench locations). The addition of texture 252 may allow the leaflet 250 to be crimped more tightly while reducing a probability of damage, and may improve the fatigue life (number of cycles in-vivo) of the leaflet.

It is understood the illustrated textures are exemplary. Leaflet texture may be of various shapes, and may vary in size, shape, and/or orientation across a surface of a leaflet. The texture features may protrude outwards (e.g., to form protrusions) or recede inwards (e.g., to form trenches), compared to a non-texture surface of a leaflet. In some instances, textures including outward protrusions advantageously is in a direction of pressure during valve closure. In some embodiments, a height of the texture 252 (e.g., a height from a trench to a peak of a protrusion) is 1-200 times the thickness of the leaflet material for height of the texture. In some embodiments, a transverse dimension (e.g., a dimension of a protrusion parallel to a plane of the leaflet) of the texture 252 is 10-12,500 times the film thickness.

Figure 3A:
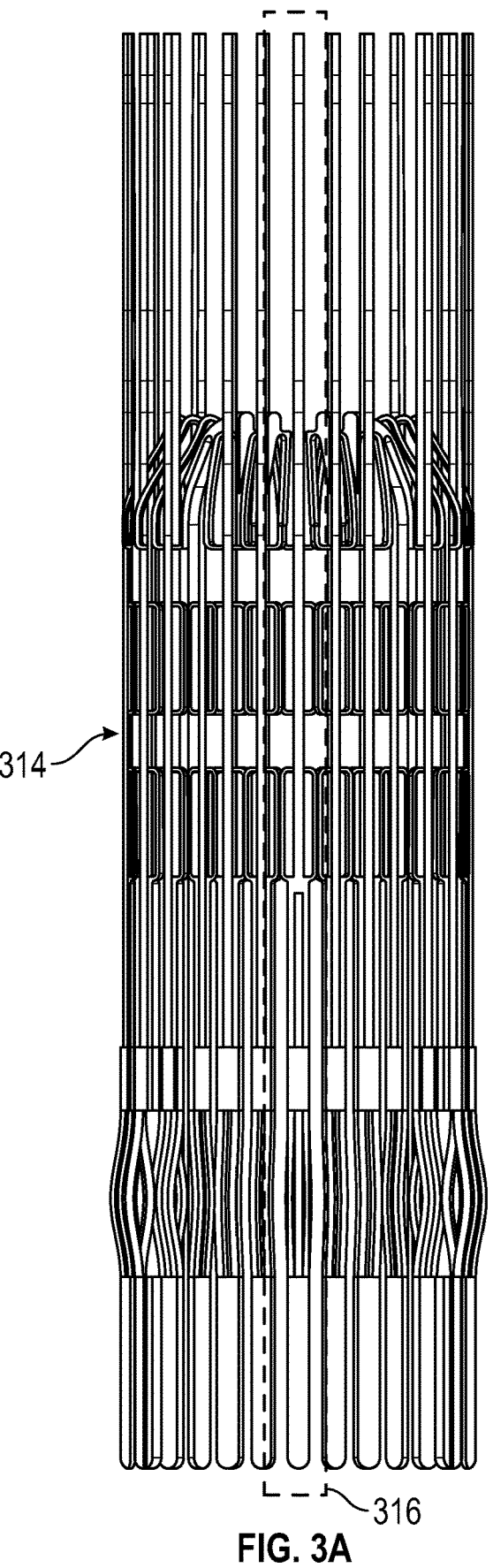
FIGS. 3A-3C illustrate an exemplary frame.

FIG. 3A illustrates an exemplary frame 314. In this example, the frame 314 is in a collapsed configuration. The frame 314 may be frame 114 in a collapsed configuration. The frame 314 may include cells 316, which may be cells 116, that are in a collapsed configuration. The frame 314 may also include anchoring prongs that are folded against the cells. Although the entire device is not shown, it is understood that the frame 314 may be included in a device in a collapsed configuration, and other elements (e.g., leaflets) of the device would collapsed accordingly. For example, the device comprises a collapsed configuration such that the device is deliverable in a catheter having a cross sectional diameter of 5-15 mm. As one example, the cross section dimension of the catheter is 8-12 mm for a valve configured for use in the tricuspid location. In some examples, the valve device may fit a catheter having a smaller diameter.

For example, the frame crimps within a catheter. As another example, the leaflets may be deformable and fit into the catheter during deliver to a heart valve. The device may be collapsed using a crimping tool, by manual force, or by drawing it into a delivery stent. Exposing the valve device to cold temperature, such as immersion in ice water or similar, prior to delivery, may aid this process. Further configurations, variations, and embodiments of the crimped frame are provided in the Appendix.

The collapse may be accomplished by forcing cells of the frame to deform. In some embodiments, the frame may include guides or features causing the film to fold in a particular way. In some embodiments, the film may fold naturally in a way that allows for collapse of the device. In some embodiments, the crimping tool may include features causing the film to fold in a particular way. The device may return to its manufactured or resting shape due to spring force from the stent frame or cells of the stent frame.

Figure 3B:
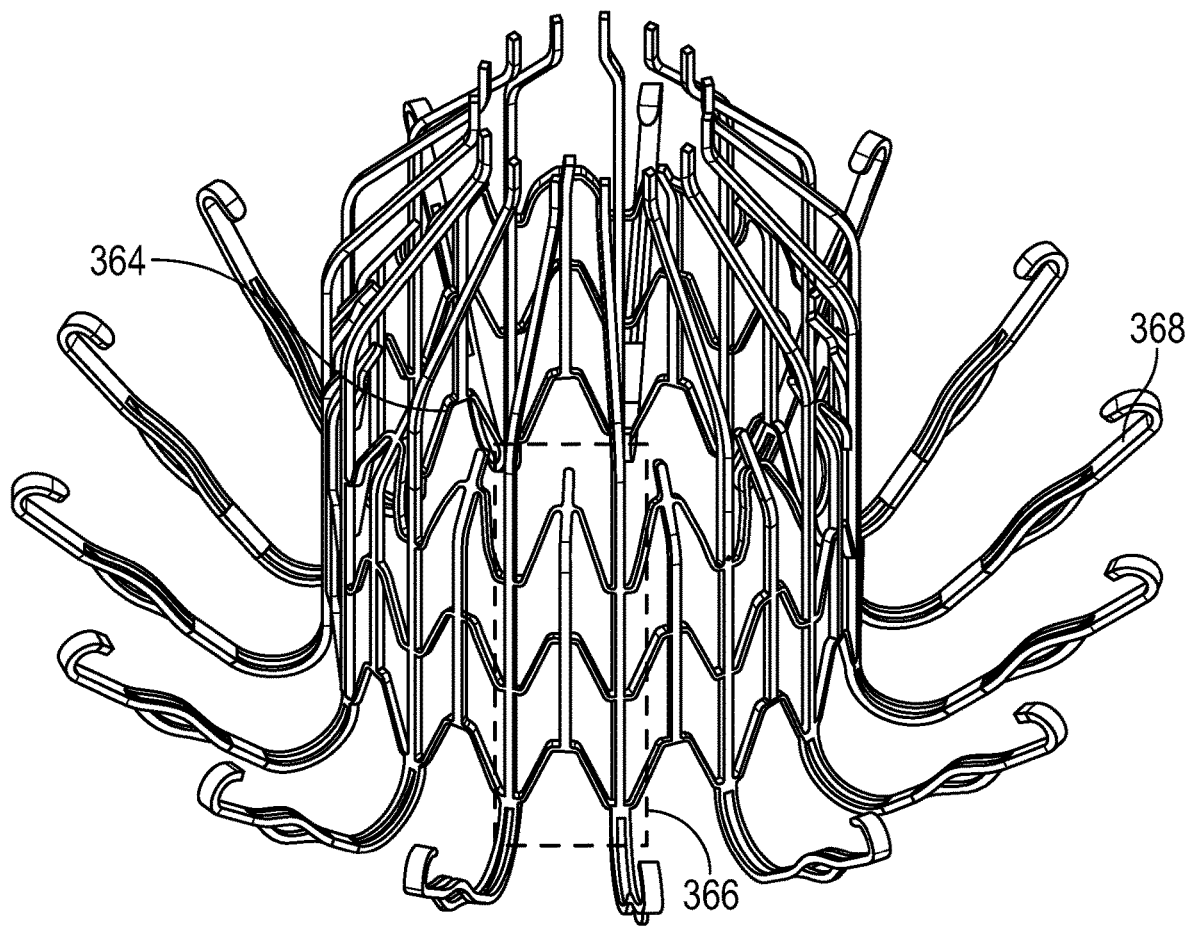

FIG. 3B illustrates an exemplary frame 364. In this example, the frame 364 is in a partially deployed configuration. The frame 364 may be frame 114 in a partially deployed configuration. Partial deployment of the disclosed valve device will be described in more detail below. The frame 364 may include cells 366 and anchoring prongs 368, which may be cells 116 and anchoring prongs 118, respectively, that are in a partially deployed configuration. In a partially deployed configuration, the cells 366 and anchoring prongs 368 may be expanded from their collapsed configurations. For example, the cells 366 may expand such that the expansion causes the diameter of the frame to increase. The anchoring prongs 368 may be at an angle between 120 and 175 degrees relative to an anchoring prong of the collapsed configuration showed in FIG. 3A (e.g., an angle 15 and 60 degrees relative to an axis from a downstream to an upstream direction along the stent frame). Although the entire device is not shown, it is understood that the frame 364 may be included in a device in a partially deployed configuration, and other elements (e.g., leaflets) of the device would be partially deployed accordingly.

Figure 3C:
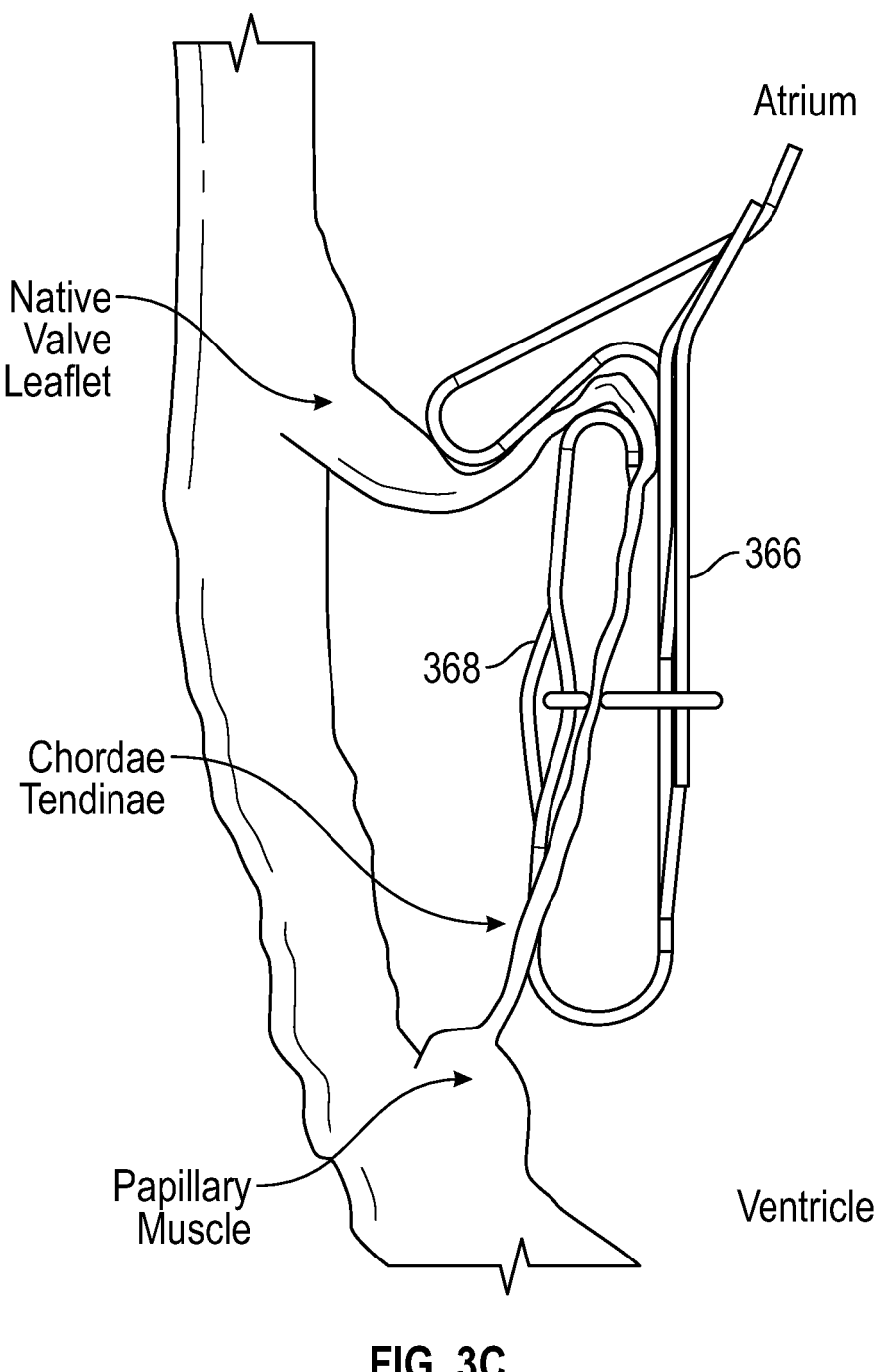

FIG. 3C illustrates an exemplary cell 366 and anchoring prong 368. In some embodiments, as illustrated, the cell 366 and anchoring prong 368 are part of a frame (e.g., frame 364) in a deployed position (for clarity, other elements of the frame are not shown). In some embodiments, upon contact with a native valve leaflet, the anchoring prong 368 of the cell 366 pinches the native valve leaflet. For example, as illustrated, the anchoring prong 368 pinches to the native valve leaflet.

Figure 4:
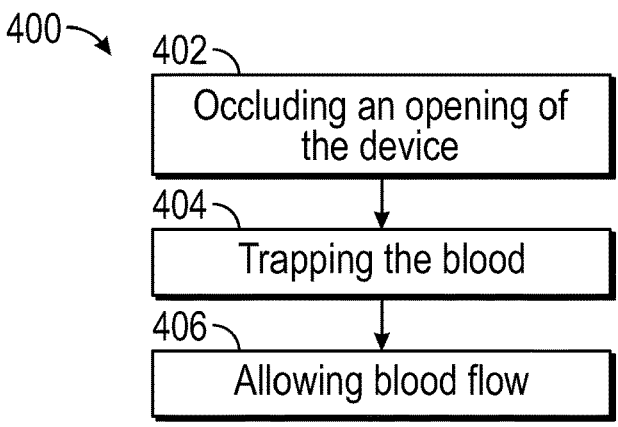
FIG. 4 illustrates an exemplary method of operating the valve device.

FIG. 4 illustrates an exemplary method 400 of operating the valve device. The method 400 may be a method of operating a replacement tricuspid valve, mitral valve, pulmonic valve, or aortic valve. In some embodiments, the method 400 describes operation of the valve device 100. The method 400 may be performed with the valve device 100 is anchored to native leaflets at a desired operating location.

Although the method 400 is illustrated as including the described steps, it is understood that different order of steps, additional steps (e.g., combination with other methods disclosed herein), or fewer steps may be included without departing from the scope of the disclosure.

In some embodiments, the method 400 includes in response to blood pumped by a heart muscle in a direction from a downstream surface to an upstream surface of a thin-film leaflet of the valve device, selectively occluding an opening of the valve device with the upstream surface (step 402). In this step, the device may be in a first configuration (e.g., closed configuration). For example, when operating a tricuspid valve device, during systole, blood is pumped from the right ventricle to the right atrium (e.g., reverse flow), and the device is occluded. As another example, when operating a mitral valve device, during systole, blood is pumped from the left ventricle to the left atrium, and the device is occluded. The configurations and exemplary advantages of the device are described with respect to FIGS. 1A-1C, 2A, and 2B. For brevity, the configurations and advantages would not be described again.

In some embodiments, the opening of the valve device is selectively occluded in response to a force from a downstream surface to an upstream surface of a thin-film leaflet of a valve device. For example, when operating an aortic valve, during diastole, blood is pumped into the left ventricle, and a force from the aorta to the left ventricle causes the opening to be selectively occluded. As another example, when operating a pulmonic valve, during diastole, blood is pumped into the right ventricle, and a force from the pulmonary artery to the right ventricle causes the opening to be selectively occluded.

In some embodiments, the method 400 includes in response to blood pumped by a heart muscle in a direction from a downstream surface to an upstream surface of a leaflet of the valve device, trapping the blood pumped by the heart muscle with the downstream surface (step 404). For example, during systole, the downstream surface of the leaflet of valve device 100 traps the reverse flowing blood. The configurations and exemplary advantages of the device are described with respect to FIGS. 1A-1C, 2A, and 2B. For brevity, the configurations and advantages would not be described again.

In some embodiments, the method 400 includes in response to blood flow in a direction from the upstream surface to the downstream surface, deforming, with a force of the blood flow, the leaflet (step 406). In this step, the device may be in a second configuration (e.g., open configuration), different from the first configuration. For example, when operating a tricuspid valve device, during diastole, blood is pumped from the right atrium to the right ventricle (e.g., forward flow), and the force of the blood flow deforms the leaflet. As another example, when operating a mitral valve device, during diastole, blood is pumped from the left atrium to the left ventricle, and the force of the blood flow deforms the leaflet. As yet another example, when operating an aortic valve, during systole, blood is pumped from the left ventricle to the aorta. As yet another example, when operating a pulmonic valve, during systole, blood is pumped from the right ventricle to the pulmonary artery. The configurations and exemplary advantages of the device are described with respect to FIGS. 1A-1C, 2A, and 2B. For brevity, the configurations and advantages would not be described again.

In some embodiments, the method 400 includes in response to blood flow in a direction from the upstream surface to the downstream surface, allowing the blood flow across the opening (step 408). For example, during diastole, the deformed leaflet allows forward flowing blood to flow across the opening of the valve device. The configurations and exemplary advantages of the device are described with respect to FIGS. 1A-1C, 2A, and 2B. For brevity, the configurations and advantages would not be described again.

In some embodiments, the method 400 may be repeated for each subsequent cardiac cycle.

Figure 5:
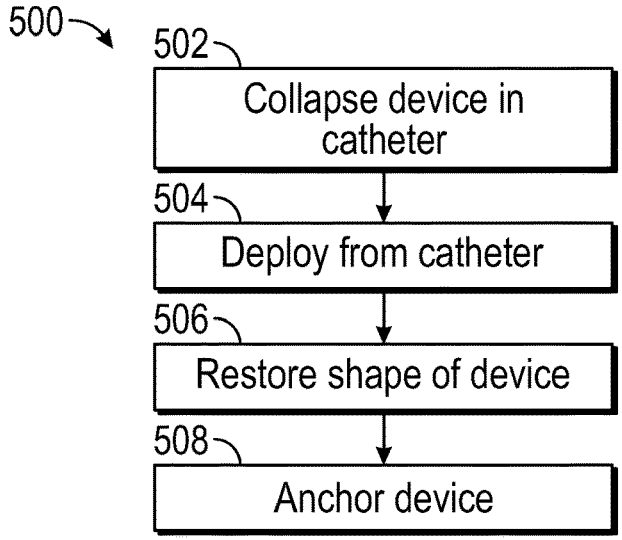
FIG. 5 illustrates an exemplary method of implanting the valve device.

FIG. 5 illustrates an exemplary method 500 of implanting the valve device. The method 500 may be a method of delivering a replacement tricuspid valve, mitral valve, pulmonic valve, or aortic valve. In some embodiments, the method 500 describes implantation of the valve device 100. The method 500 may be performed to anchor the valve device to native leaflets at a desired operating location.

Although the method 500 is illustrated as including the described steps, it is understood that different order of steps, additional steps (e.g., combination with other methods disclosed herein), or fewer steps may be included without departing from the scope of the disclosure. For example, steps 506 and 508 may be performed while step 504 is being performed (e.g., while the device is being deployed, the shape of the device is restored, and the device is anchored).

In some embodiments, the method 500 includes collapsing the valve device to fit into a catheter (step 502). For example, when implanting the valve device in the tricuspid location, the valve device is collapsed into the catheter before being transported toward the right atrium for implantation, as described herein. The valve device may be transported using a trans-jugular approach through the superior vena cava or a trans-femoral approach through the inferior vena cava, and the collapsed valve is advanced through the tricuspid valve into the right ventricle. A similar process, using a trans-femoral, trans-septal delivery route, could be used for delivery in the mitral location.

When the valve device is loaded in a catheter, the valve device may be collapsed to fit into the catheter in a shape that allows for efficient transportation of the valve device to a desired operating location. Additional configurations and exemplary advantages of the device at this step are described with respect to FIGS. 1A-1C, 2A-2F, and 3A-3C. For brevity, the configurations and advantages would not be described again.

In some embodiments, the method 500 includes deploying the valve device from the catheter (step 504). For example, the valve device is partially deployed (e.g., released) from the catheter. The valve device may be exiting the catheter near its operating location.

During or after deployment of the valve device, using imaging guidance (e.g., fluoroscopy or echocardiogram), the anchoring prongs may be positioned against the underside of native (e.g., tricuspid, mitral) leaflets. During this process, steering and/or rotation of the catheter may be used to assist the prongs in finding a position between chordae of the native valve such that all prongs are seated properly. The catheter may be slowly retracted after the valve device is positioned.

Additional configurations and exemplary advantages of the device at this step are described with respect to FIGS. 1A-1C, 2A-2F, and 3A-3C. For brevity, the configurations and advantages would not be described again.

In some embodiments, the method 500 includes in response to deploying the valve device from the catheter, restoring a shape of the valve device (step 506). For example, the restored shape is a resting shape of the valve device, as described herein. With the anchoring prongs seated, the frame may expand. The frame may be either balloon-expanded or self-expanding. Restoring the shape of the valve device may include releasing the anchoring prongs. For example, the valve device may begin to return to its resting shape, the anchoring prongs return to its resting configuration (e.g., between 90 and 180 degrees relative to the frame), and the leaflets return to its manufactured shape (e.g., leaflets in a closed configuration). Additional configurations and exemplary advantages of the device at this step are described with respect to FIGS. 1A-1C, 2A-2F, and 3A-3C. For brevity, the configurations and advantages would not be described again.

In some embodiments, the method 500 includes anchoring the valve device to a native leaflet comprising pinching the native leaflet between an anchoring prong and a frame of the valve device (step 508). For example, as the frame expands, extension-limiting takes effect, causing tips of the anchoring prongs to rotate inward toward the center of the valve device. Further expansion of the frame pinches the native tricuspid leaflets between the frame and the anchoring prongs, thus securing the device in place. Additional configurations and exemplary advantages of the device at this step are described with respect to FIGS. 1A-1C, 2A-2F, and 3A-3C. For brevity, the configurations and advantages would not be described again.

Although the method 500 is described with respect to anchoring of one valve device, it is understood that multiple device may be loaded into one or more catheters, deployed, or anchored concurrently without departing from the scope of the disclosure.

In some embodiments, after the valve device anchored, the valve frame is released from the catheter, and the catheter is withdrawn.

Figure 6:
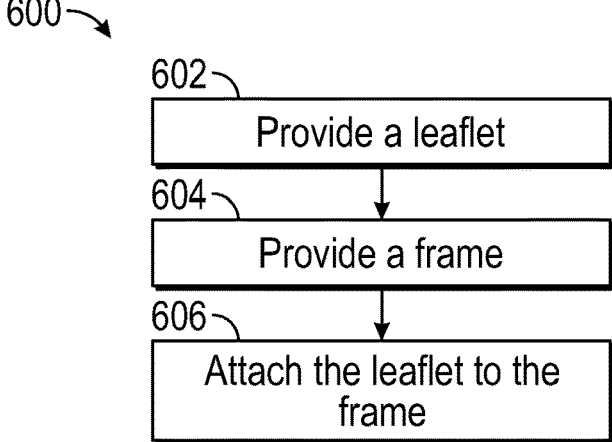
FIG. 6 illustrates an exemplary method of manufacturing the valve device.

FIG. 6 illustrates an exemplary method 600 of manufacturing the valve device. The method 600 may be a method of manufacturing a replacement tricuspid valve, mitral valve, pulmonic valve, or aortic valve. In some embodiments, the method 600 describes the manufacturing of the valve device 100.

Although the method 600 is illustrated as including the described steps, it is understood that different order of steps, additional steps (e.g., combination with other methods disclosed herein), or fewer steps may be included without departing from the scope of the disclosure. For example, steps 602 and 604 may be performed in parallel (e.g., the leaflet and the frame are provided at a same time).

In some embodiments, the method 600 includes providing a three-dimensional thin-film leaflet comprising: a downstream surface to trap blood pumped by a heart muscle, and an upstream surface to selectively occlude an opening of the valve device when the leaflet's downstream surfaces trap blood pumped by the heart muscle (step 602). The three-dimensional thin-film leaflet may comprise one of biocompatible alloy, polymer, and composite structure. Providing the three-dimensional thin-film leaflet further may also include forming stress relief features on the leaflet using at least one of laser cutting, photo-lithography, vapor deposition, hot-working, cold-working, photo-etching, and mechanical cutting. The three-dimensional thin-film leaflet may be fabricated as one piece using vacuum deposition, PVD, or CVD. The three-dimensional thin-film leaflet may be formed by physical vapor deposition of at least one of an alloy and a polymer. The alloy may be superelastic Nitinol. The polymer may be Kevlar, Parylene, PTFE, or FEP. The three-dimensional thin-film leaflet may be formed by at least one of dipping, painting, and molding. The three-dimensional thin-film leaflet may be formed with a tool that molds the shape of the leaflet. Additional features and exemplary advantages of the leaflet are described with respect to FIGS. 1A-1C, 2A-2F, and 3A-3C. For brevity, the features and advantages would not be described again.

In some embodiments, the method 600 includes providing a frame defining an opening of the valve device, wherein the frame comprises a plurality of cells (step 604). For example, the frame may be frame 114 comprising cells 116. The frame or cells may be formed by laser cutting. In some embodiments, the frame may include anchoring prongs, as described herein; the anchoring prongs may be formed with the frame or separately formed and then attached to the frame. One or more cords, as described herein, may be provided and connected to the anchoring prongs; the number of the cords and connection points may depend on the configuration of the valve device. For example, the cord may comprise at least one of a wire rope of one of Nitinol, a wire rope of a non-Nitinol biocompatible alloy, a solid or multi-filar cord of a PTFE, a solid or multi-filar Kevlar cord, and a non-PTFE and a no-Kevlar solid or multi-filar cord.

In some embodiments, the frame may include skirts, as described herein; the skirts may be formed with the frame or separately formed and then attached to the frame. For example, the method 600 may include attaching a skirt to the frame and outside the opening to stop blood (e.g., pumped by the heart muscle) in a direction from the downstream surface to the upstream surface outside the opening. In some embodiments, the skirt may stop blood from the upstream surface to the downstream surface outside the opening. Additional features and exemplary advantages of the frame are described with respect to FIGS. 1A-1C, 2A-2F, and 3A-3C. For brevity, the features and advantages would not be described again.

In some embodiments, the method 600 includes attaching the leaflet to the frame (step 606). For example, the leaflet may be welded, sewn, clamped, or glued to attach to the frame. Additional features and exemplary advantages of the device are described with respect to FIGS. 1A-1C, 2A-2F, and 3A-3C. For brevity, the features and advantages would not be described again.

In one aspect, a valve device, comprises: an opening, and a leaflet comprising: a downstream surface to trap blood pumped by a heart muscle, and an upstream surface to selectively occlude the opening when the leaflet's downstream surfaces trap blood pumped by the heart muscle.

In some aspects of the above device, the leaflet is a three-dimensional thin-film leaflet.

In some aspects of the above devices, the upstream surface comprises a dome portion.

In some aspects of the above devices, a shape of the leaflet includes a plurality of profiles, each profile includes dimensions of an interfacing surface height, an outer cylindrical surface height, and a profile slope angle, and the profile slope angle is associated with geometries of the dome portion.

In some aspects of the above devices, the interfacing surface height is 2-10 mm, the outer cylindrical surface height is 3-25 mm, and the profile slope angle is −45 to 45 degrees.

In some aspects of the above devices, the shape of the leaflet includes a dimension of an average slope associated with an average of at least some of the profile slope angles along at least a part of a depth of the leaflet, and the average slope is 0 to 45 degrees.

In some aspects of the above devices, the device consists three leaflets.

In some aspects of the above devices, the device further comprises a second leaflet, wherein the leaflets' upstream surfaces collectively occlude the opening when the leaflets are in a first configuration, and the upstream surfaces do not collectively occlude the opening when the leaflets are in a second configuration.

In some aspects of the above devices, each leaflet comprises an interfacing surface that, while the leaflets occlude the opening, contacts an adjacent leaflet's interfacing surface.

In some aspects of the above devices, the interfacing surface has a height of 2-10 mm.

In some aspects of the above devices, the interfacing surface comprises ridges and troughs.

In some aspects of the above devices, the ridges and troughs are parallel to a direction from the upstream surface to the downstream surface.

In some aspects of the above devices, the interfacing surface comprises dimples located periodically along the interfacing surface.

In some aspects of the above devices, the interfacing surface comprises cuts.

In some aspects of the above devices, a thickness along a surface of the leaflet is non-uniformed.

In some aspects of the above devices, the device further comprises a frame, wherein a portion of the leaflet attaches to the frame, the portion comprising a non-uniform thickness.

In some aspects of the above devices, the leaflet has a thickness of 5-250 μm.

In some aspects of the above devices, the device comprises a collapsed configuration such that the device in the collapsed configuration is deliverable in a catheter having a cross sectional diameter of 5-15 mm.

In some aspects of the above devices, the leaflet comprises at least one of biocompatible alloy, polymer, and composite structure.

In some aspects of the above devices, the leaflet is fabricated using vacuum deposition, PVD, or CVD.

In some aspects of the above devices, the leaflet comprises: a first configuration in response to a force from the downstream side to the upstream side, and a second configuration in response to a force from the upstream side to the downstream side.

In some aspects of the above devices, the first configuration is a closed configuration and the second configuration is an open configuration.

In some aspects of the above devices, the force from the downstream side to the upstream side includes a force generated by an increase of the blood being trapped.

In some aspects of the above devices, the leaflet collapses in response to the force from the upstream side to the downstream side.

In some aspects of the above devices, the leaflet returns toward a manufactured shape in response to an increase of the blood being trapped.

In some aspects of the above devices, the leaflet further includes stress relief features.

In some aspects of the above devices, the stress relief features are formed using at least one of laser cutting, photo-lithography, vapor deposition, hot-working, cold-working, photo-etching, and mechanical cutting.

In some aspects of the above devices, the leaflet is deformable under applied pressure and return to a manufactured shape after the pressure is removed.

In some aspects of the above devices, the leaflet is formed by physical vapor deposition of at least one of an alloy and a polymer.

In some aspects of the above devices, the alloy is super-elastic Nitinol.

In some aspects of the above devices, the polymer is Kevlar, Parylene, PTFE, or FEP.

In some aspects of the above devices, the leaflet is formed by at least one of dipping, painting, and molding.

In some aspects of the above devices, the downstream surface is a domed surface along one of radial and lateral directions to reduce at least one of stress and stasis.

In some aspects of the above devices, the device further comprises a frame defining the opening, wherein the leaflet is attached to the frame.

In some aspects of the above devices, the device further comprises a skirt attached to the frame and outside the opening to occlude blood pumped by the heart muscle in a direction from the downstream surface to the upstream surface outside the opening.

In some aspects of the above devices, the frame is cylindrical and a portion of the attached leaflet matches a contour of the frame.

In some aspects of the above devices, an interfacing surface is oriented in a direction parallel to a central axis of the device.

In some aspects of the above devices, the frame is a stent frame having anchoring prongs to maintain the device at a native valve location.

In some aspects of the above devices, the frame crimps within a catheter.

In some aspects of the above devices, the anchoring prongs are in a pinching position upon contact with an underside of native leaflets.

In some aspects of the above devices, the anchoring prongs are configured to draw a valve annulus toward a center of the opening.

In some aspects of the above devices, the stent frame further includes a cord connecting the anchoring prongs, the cord to tighten and pull the anchoring prongs toward the frame as the frame expands.

In some aspects of the above devices, the cord is connected to three anchoring prongs.

In some aspects of the above devices, the device further comprises a second cord connected to three second anchoring prongs, each of the second anchoring prongs positioned on the frame and adjacent to a first anchoring prong.

In some aspects of the above devices, the cord comprises at least one of a wire rope of one of Nitinol, a wire rope of a non-Nitinol biocompatible alloy, a solid or multi-filar cord of a PTFE, a solid or multi-filar Kevlar cord, and a non-PTFE and a no-Kevlar solid or multi-filar cord.

In some aspects of the above devices, the device further comprises cord attachment points between adjacent anchoring prongs of a set of anchoring prongs.

In some aspects of the above devices, the anchoring prongs are equally-spaced along a circumference of the frame.

In some aspects of the above devices, the frame comprises a plurality of collapsible cells.

In some aspects of the above devices, the frame is created by laser cutting.

In some aspects of the above devices, the frame is balloon-expandable.

In one aspect, a method of operating an artificial valve, comprising: in response to blood pumped by a heart muscle in a direction from a downstream surface to an upstream surface of a thin-film leaflet of the artificial valve: selectively occluding an opening of the artificial valve with the upstream surface, and trapping the blood pumped by the heart muscle with the downstream surface; and in response to blood flow in a direction from the upstream surface to the downstream surface: deforming, with a force of the blood flow, the leaflet, and allowing the blood flow across the opening.

In some aspects of the above method, the artificial valve is the above devices.

In one aspect, a method of implanting a valve device, comprising: collapsing the valve device to fit into a catheter; deploying the valve device from the catheter; in response to deploying the valve device from the catheter, restoring a shape of the valve device; and anchoring the valve device to a native leaflet comprising pinching the native leaflet between an anchoring prong and a frame of the valve device.

In some aspects of the above method, the valve device is the above devices.

In one aspect, a method of manufacturing a valve device, comprising: providing a three-dimensional thin-film leaflet comprising: a downstream surface to trap blood pumped by a heart muscle, and an upstream surface to selectively occlude an opening of the valve device when the leaflet's downstream surfaces trap blood pumped by the heart muscle; providing a frame defining an opening of the valve device, wherein the frame comprises a plurality of cells; and attaching the leaflet to the frame.

In some aspects of the above method, providing the three-dimensional thin-film leaflet further comprises fabricating the leaflet using at least one of biocompatible alloy, polymer, and composite structure.

In some aspects of the above methods, providing the three-dimensional thin-film leaflet further comprises fabricating the leaflet using vacuum deposition, PVD, or CVD.

In some aspects of the above methods, providing the three-dimensional thin-film leaflet further comprises forming stress relief features on the leaflet using at least one of laser cutting, photo-lithography, vapor deposition, hot-working, cold-working, photo-etching, and mechanical cutting.

In some aspects of the above methods, providing the three-dimensional thin-film leaflet further comprises fabricating the leaflet using physical vapor deposition of at least one of an alloy and a polymer.

In some aspects of the above methods, the alloy is superelastic Nitinol.

In some aspects of the above methods, the polymer is Kevlar, Parylene, PTFE, or FEP.

In some aspects of the above methods, providing the three-dimensional thin-film leaflet further comprises fabricating the leaflet using at least one of dipping, painting, and molding.

In some aspects of the above methods, the method further comprises attaching a skirt to the frame outside the opening to stop blood pumped by the heart muscle in a direction from the downstream surface to the upstream surface outside the opening.

In some aspects of the above methods, providing the frame further comprises providing anchoring prongs on the frame.

In some aspects of the above methods, the method further comprises connecting a cord to the anchoring prongs.

In some aspects of the above methods, the cord comprises at least one of a wire rope of one of Nitinol, a wire rope of a non-Nitinol biocompatible alloy, a solid or multi-filar cord of a PTFE, a solid or multi-filar Kevlar cord, and a non-PTFE and a no-Kevlar solid or multi-filar cord.

In some aspects of the above methods, providing the frame further comprises laser cutting to form the frame.

In some aspects of the above methods, attaching the leaflet to the frame further comprises at least one of welding, sewing, clamping, and gluing the leaflet to the frame.

In some aspects of the above methods, the valve device is the above device.

Although the disclosed embodiments have been fully described with reference to the accompanying drawings, it is to be noted that various changes and modifications will become apparent to those skilled in the art. Such changes and modifications are to be understood as being included within the scope of the disclosed embodiments as defined by the appended claims.

The terminology used in the description of the various described embodiments herein is for the purpose of describing particular embodiments only and is not intended to be limiting. As used in the description of the various described embodiments and the appended claims, the singular forms "a", "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

We claim:

1. A valve device, comprising:
an opening,
a leaflet comprising:
a downstream surface to trap blood pumped by a heart muscle, and
an upstream surface to selectively occlude the opening when the leaflet's downstream surfaces trap blood pumped by the heart muscle, wherein the upstream surface comprises a dome portion,
wherein:
the leaflet is a three-dimensional thin-film leaflet,
a shape of the leaflet includes a plurality of profiles, each profile includes dimensions of an interfacing surface height, an outer cylindrical surface height, and a profile slope angle, and
the profile slope angle is associated with geometries of the dome portion, and
a frame defining the opening and comprising anchoring prongs, wherein:
the leaflet is attached to the frame, and
when the frame is in a partially deployed configuration, the anchoring prongs are at an angle between 15 and 60 degrees relative to an axis from the downstream surface to the upstream surface.

2. The device of claim 1, wherein the interfacing surface height is 2-10 mm, the outer cylindrical surface height is 3-25 mm, and the profile slope angle is −45 to 45 degrees.

3. The device of claim 1, further comprising a second leaflet, wherein the leaflets' upstream surfaces collectively occlude the opening when the leaflets are in a first configuration, and the upstream surfaces do not collectively occlude the opening when the leaflets are in a second configuration.

4. The device of claim 3, wherein each leaflet comprises an interfacing surface that, while the leaflets occlude the opening, contacts an adjacent leaflet's interfacing surface.

5. The device of claim 1, wherein the leaflet has a thickness of 5-25 $\mu$m.

6. The device of claim 1, wherein the device comprises a collapsed configuration such that the device in the collapsed configuration is deliverable in a catheter having a cross sectional diameter of 5-15 mm.

7. The device of claim 1, wherein the leaflet comprises:
a first configuration in response to a force from the downstream side to the upstream side, and
a second configuration in response to a force from the upstream side to the downstream side.

8. The device of claim 7, wherein the force from the downstream side to the upstream side includes a force generated by an increase of the blood being trapped.

9. The device of claim 7, wherein the leaflet collapses in response to the force from the upstream side to the downstream side.

10. The device of claim 1, wherein the leaflet returns toward an inflated shape in response to an increase of the blood being trapped.

11. The device of claim 1, wherein:
the anchoring prongs maintain the device at a native valve location, and
the anchoring prongs are in a pinching position upon contact with an underside of native leaflets.

12. The device of claim 1, further comprising a cord connecting the anchoring prongs, the cord configured to tighten and pull the anchoring prongs toward the frame as the frame expands from a collapsed configuration such that the anchoring prongs are in a pinching position upon contact with an underside of native leaflets.

13. A method of operating an artificial valve comprising:
deploying the artificial valve;
in response to blood pumped by a heart muscle in a direction from a downstream surface to an upstream surface of a thin-film leaflet of the artificial valve:
selectively occluding an opening of the artificial valve with the upstream surface, wherein the upstream surface comprises a dome portion, and
trapping the blood pumped by the heart muscle with the downstream surface; and in response to blood flow in a direction from the upstream surface to the downstream surface:

deforming, with a force of the blood flow, the leaflet, and allowing the blood flow across the opening, wherein:

the leaflet is a three-dimensional thin-film leaflet, a shape of the leaflet includes a plurality of profiles, each profile includes dimensions of an interfacing surface height, an outer cylindrical surface height, and a profile slope angle, and the profile slope angle is associated with geometries of the dome portion, and deploying the artificial valve comprises configuring a frame of the artificial valve to a partially deployed configuration, wherein when the frame is in the partially deployed configuration, anchoring prongs of the frame are at an angle between 15 and 60 degrees relative to an axis from the downstream surface to the upstream surface.

14. The method of claim 13, wherein deploying the artificial valve further comprises tightening a cord of the artificial valve connecting the anchoring prongs to pull the anchoring prongs toward the frame as the frame expands from a collapsed configuration such that the anchoring prongs are in a pinching position upon contact with an underside of native leaflets.

15. A method of manufacturing a valve device comprising:

fabricating a three-dimensional thin-film leaflet via vacuum deposition, PVD, CVD, or any combination thereof, wherein the thin-film leaflet comprises:

a downstream surface, and an upstream surface, wherein the upstream surface comprises a dome portion, wherein:

a shape of the leaflet includes a plurality of profiles, each profile includes dimensions of an interfacing surface height, an outer cylindrical surface height, and a profile slope angle, and the profile slope angle is associated with geometries of the dome portion;

providing a plurality of cells;

forming a frame by coupling the plurality of cells, wherein the frame defines an opening of the valve device; and attaching the leaflet to the frame.

16. The method of claim 15, further comprising shaping the leaflet via the vacuum deposition, the PVD, the CVD, or any combination thereof.

17. The method of claim 15, wherein one of more the cells comprise anchoring prongs, the method further comprising providing a cord connecting the anchoring prongs.

\* \* \* \* \*